(12) United States Patent
Mangual-Soto et al.

(10) Patent No.: US 12,128,240 B2
(45) Date of Patent: Oct. 29, 2024

(54) METHOD AND SYSTEM FOR BIVENTRICULAR OR LEFT VENTRICULAR PACING

(71) Applicant: Pacesetter, Inc., Sylmar, CA (US)

(72) Inventors: Jan O. Mangual-Soto, Rho (IT); Nima Badie, Berkeley, CA (US); Luke C. McSpadden, Los Angeles, CA (US)

(73) Assignee: Pacesetter, Inc., Sylmar (CA)

( * ) Notice: Subject to any disclaimer, the term of this patent is extended or adjusted under 35 U.S.C. 154(b) by 324 days.

(21) Appl. No.: 17/586,845

(22) Filed: Jan. 28, 2022

(65) Prior Publication Data

US 2022/0288399 A1 Sep. 15, 2022

Related U.S. Application Data

(60) Provisional application No. 63/159,494, filed on Mar. 11, 2021.

(51) Int. Cl.
*A61N 1/368* (2006.01)
*A61N 1/05* (2006.01)
*A61N 1/36* (2006.01)

(52) U.S. Cl.
CPC ....... *A61N 1/36843* (2017.08); *A61N 1/0563* (2013.01); *A61N 1/36167* (2013.01); *A61N 1/3686* (2013.01)

(58) Field of Classification Search
CPC .............. A61N 1/0563; A61N 1/36167; A61N 1/3627; A61N 1/36507; A61N 1/36843;
(Continued)

(56) References Cited

U.S. PATENT DOCUMENTS

| 8,467,871 B2 | 6/2013 | Maskara |
| 2003/0130702 A1 | 7/2003 | Kramer et al. |

(Continued)

FOREIGN PATENT DOCUMENTS

CN 109771824 A 5/2019

OTHER PUBLICATIONS

Thibault et al., "Left Ventricular Versus Simultaneous Biventricular Pacing in Patients With Heart Failure and a QRS Complex ≥120 Milliseconds", Circulation 2011; 124: 2874-81; 8 pages.
(Continued)

*Primary Examiner* — Brian T Gedeon
(74) *Attorney, Agent, or Firm* — Dean D. Small; The Small Patent Law Group, LLC

(57) ABSTRACT

A system and method have at least one implantable lead comprising a right ventricular (RV) electrode and one or more left ventricular (LV) electrodes, at least one processor, and a memory coupled to the at least one processor. The memory stores program instructions. The program instructions are executable by the at least one processor to determine a right ventricular to left ventricular (RV-LV) conduction time representative of a conduction time between a right ventricular (RV) paced event and one or more responsive left ventricular (LV) sensed events, determine a left ventricular to right ventricular (LV-RV) conduction time representative of a conduction time between one or more LV paced event and an RV sensed events, calculate a relation between the RV-LV conduction time and the LV-RV conduction time, and set a pacing mode of an implantable medical device to one of i) a biventricular (BiV) pacing mode and ii) an LV only pacing mode based on the relation between the RV-LV conduction time and the LV-RV conduction time.

20 Claims, 8 Drawing Sheets

(58) Field of Classification Search
CPC .... A61N 1/3686; A61N 1/3688; A61B 5/287; A61B 5/308; A61B 5/361; A61B 5/363
See application file for complete search history.

(56) References Cited

U.S. PATENT DOCUMENTS

| | | | |
|---|---|---|---|
| 2004/0088017 A1* | 5/2004 | Sharma | A61N 1/3629 607/25 |
| 2008/0269823 A1 | 10/2008 | Burnes et al. | |
| 2010/0087889 A1 | 4/2010 | Maskara et al. | |
| 2011/0022112 A1 | 1/2011 | Min | |
| 2011/0137369 A1 | 6/2011 | Ryu et al. | |
| 2013/0261687 A1 | 10/2013 | Xi et al. | |
| 2017/0340885 A1 | 11/2017 | Sambelashvili | |
| 2017/0340887 A1 | 11/2017 | Engles et al. | |
| 2019/0091478 A1 | 3/2019 | Wisnoskey et al. | |
| 2020/0078591 A1 | 3/2020 | Min et al. | |
| 2020/0188677 A1 | 6/2020 | An et al. | |

OTHER PUBLICATIONS

Extended European Search Report for corresponding EP Application No. 22156475 dated Jul. 8, 2022.

* cited by examiner

METHOD AND SYSTEM FOR BIVENTRICULAR OR LEFT VENTRICULAR PACING

RELATED APPLICATION

This application claims priority to U.S. Provisional Application Ser. No. 63/159,494, filed Mar. 11, 2021, which is incorporated herein by reference in their entirety.

FIELD OF THE INVENTION

Embodiments herein generally relate to implantable medical devices, and more particularly to determining to implement biventricular (BiV) pacing or left ventricular (LV) only pacing.

BACKGROUND OF THE INVENTION

Advances in cardiac resynchronization therapy (CRT) devices, left ventricular (LV) lead design, and dynamic pacing delay algorithms have resulted in improved patient outcome. Optimal AV delays (AVD) can improve electrical synchrony, and, if adequately timed, may result in fusion pacing. During fusion pacing, the intrinsic conduction wavefront and device pacing are timely fused to produce an enhanced depolarization of the ventricles and increased cardiac output. However, both the LV and right ventricular (RV) chambers may not require pacing to achieve the optimal response to CRT in all patients. Choosing which chamber(s) to pace may improve outcomes and prolong battery longevity.

Various approaches have proposed to select between biventricular (BiV) and LV only pacing (e.g., LV single site (LVSS) pacing or LV multipoint pacing (MPP)). However, a need remains for further improvements when selecting between biventricular and LV only pacing. Adequate selection between BiV and LV only pacing is very important as LV only pacing may still be effective in individuals who are nonresponsive to BiV pacing. In addition, LV only pacing reduces costs, and limits procedure time. Moreover, LV only pacing may avoid the deleterious effects of RV pacing while extending battery life.

In some instances, it has been shown that LV only pacing was not superior for certain individuals to BiV pacing, while in other instances, it has been shown that non-responders to BiV may still respond favorably to LV only pacing. The latter circumstance highlights the need of an algorithm that can determine which chamber(s) to pace.

Therefore, a need remains for improved methods and systems for determining whether to implement BiV pacing or LV only pacing.

SUMMARY

In accordance with embodiments herein, a system is provided. The system has at least one implantable lead comprising a right ventricular (RV) electrode and one or more left ventricular (LV) electrodes, at least one processor, and a memory coupled to the at least one processor. The memory stores program instructions. The program instructions are executable by the at least one processor to: determine at least one of: i) a right ventricular to left ventricular (RV-LV) conduction time representative of a conduction time between a right ventricular (RV) paced or sensed event and one or more responsive left ventricular (LV) sensed events; or ii) a left ventricular to right ventricular (LV-RV) conduction time representative of a conduction time between one or more LV paced or sensed events and an RV sensed event. The at least one processor calculates a relation between a threshold and the at least one of the RV-LV conduction time or LV-RV conduction time; and sets a pacing mode of an implantable medical device to one of i) a biventricular (BiV) pacing mode and ii) an LV only pacing mode based on the relation.

Optionally, the at least one processor may be further configured to: when calculating the relation, compare the threshold to at least one of i) the RV-LV conduction time, ii) the LV-RV conduction time, or iii) a difference between the RV-LV and LV-RV conduction times; and when setting the pacing mode, to perform at least one of: i) set the pacing mode to the BiV pacing mode when the difference exceeds the threshold and to set the pacing mode to the LV only pacing mode when the difference equals or is below the threshold; ii) set the pacing mode to the BiV pacing mode when the RV-LV conduction time is below the threshold and to set the pacing mode to the LV only pacing mode when the difference equals or exceeds the threshold; or iii) set the pacing mode to the BiV pacing mode when the LV-RV conduction time is below the threshold and to set the pacing mode to the LV only pacing mode when the difference equals or exceeds the threshold.

Optionally, the at least one processor may be further configured to determine both of the RV-LV conduction time and the LV-RV conduction time and calculate, as the relation, a mathematical relation between the RV-LV conduction time and the LV-RV conduction time, the pacing mode set based on the mathematical relation.

Optionally, the RV-LV conduction time represents the conduction time between an RV paced event and an LV sensed event (RVp-LVs), wherein the LV-RV conduction time represents the conduction time between an LV paced event and an RV sensed event (LVp-RVs), and wherein the relation represents a difference between the RVp-LVs conduction time and the LVp-RVs conduction time.

Optionally, the at least one processor may be further configured to calculate, as the relation, a mathematical relation between the RV-LV conduction time and the LV-RV conduction time, the pacing mode set based on the mathematical relation. The mathematical relation may represent a difference between the RV-LV conduction time and the LV-RV conduction time. The at least one processor may be further configured to compare the difference to a threshold and to set the pacing mode to the BiV pacing mode when the difference is below the threshold and to set the pacing mode to the LV only pacing mode when the difference equals or exceeds the threshold.

Optionally, they system may comprise an LV lead having multiple LV electrodes configured to detect LV sensed events and to deliver LV paced events. The at least one processor may be further configured to measure intrinsic RV/LV intervals between an RV intrinsic event, measured at the RV electrode, and LV intrinsic events, measured at the corresponding LV electrodes, and based on the measured intrinsic RV/LV intervals, select one of the LV electrodes as an LV pace/sense site to use to determine the RV-LV conduction time and the LV-RV conduction time. The LV pace/sense site selected may represent the one of the LV electrodes having a longest one of the RV-LV intrinsic conduction times. The LV pace/sense site may represent a site of latest LV activation within the multiple LV electrodes.

Optionally, the at least one processor may be further configured to identify a site of latest LV activation to be utilized to determine the RV-LV conduction time and the LV-RV conduction time. During the LV only pacing mode, the at least one processor may be configured to not pace in the RV. The at least one processor may be further configured to time delivery of RV and LV pacing pulses in the BiV pacing mode in a fusion timing manner with intrinsic conduction in the RA. The at least one processor may be further configured to time delivery of pacing pulses in the LV only pacing mode in a fusion timing manner with intrinsic conduction from the RV apex along the LV.

In accordance with embodiments herein, a computer implemented arrhythmia detection method is provided. The method is under control of one or more processors configured with specific executable instructions. The method determines at least one of: i) a right ventricular to left ventricular (RV-LV) conduction time representative of a conduction time between a right ventricular (RV) paced or sensed event and one or more responsive left ventricular (LV) sensed events; or ii) a left ventricular to right ventricular (LV-RV) conduction time representative of a conduction time between one or more LV paced or sensed events and an RV sensed event. The method calculates a relation between a threshold and the at least one of the RV-LV conduction time or LV-RV conduction time; and setting a pacing mode of an implantable medical device (IMD) to a select one of i) a biventricular (BiV) pacing mode and ii) an LV only pacing mode based on the relation.

Optionally, the method further comprises, when calculating the relation, comparing the threshold to at least one of i) the RV-LV conduction time, ii) the LV-RV conduction time, or iii) a difference between the RV-LV and LV-RV conduction times; and when setting the pacing mode, to perform at least one of: i) setting the pacing mode to the BiV pacing mode when the difference exceeds the threshold and to set the pacing mode to the LV only pacing mode when the difference equals or is below the threshold; ii) setting the pacing mode to the BiV pacing mode when the RV-LV conduction time is below the threshold and to set the pacing mode to the LV only pacing mode when the difference equals or exceeds the threshold; or iii) setting the pacing mode to the BiV pacing mode when the LV-RV conduction time is below the threshold and to set the pacing mode to the LV only pacing mode when the difference equals or exceeds the threshold.

Optionally, the method further comprises determining both of the RV-LV conduction time and the LV-RV conduction time and calculating, as the relation, a mathematical relation between the RV-LV conduction time and the LV-RV conduction time, the pacing mode set based on the mathematical relation.

Optionally, the method may calculate, as the relation, a mathematical relation between the RV-LV conduction time and the LV-RV conduction time, the pacing mode set based on the mathematical relation. The mathematical relation may represent a difference between the RV-LV conduction time and the LV-RV conduction time. The method may further comprise comparing the difference to a threshold and to set the pacing mode to the BiV pacing mode when the difference is below the threshold and setting the pacing mode to the LV only pacing mode when the difference equals or exceeds the threshold.

Optionally, the method may detect an RV intrinsic event, may detect LV intrinsic events, associated with the RV intrinsic event, utilizing multiple LV electrodes. The method may measure intrinsic RV-LV intervals between the RV intrinsic event, measured at the RV electrode, and the LV intrinsic events, measured at the corresponding LV electrodes, and based on the measured intrinsic RV-LV intervals, may set a configuration mode of the IMD to utilize one of the LV electrodes as an LV pace/sense site when determining the RV-LV conduction time and the LV-RV conduction time.

Optionally, the LV pace/sense site selected may represent the one of the LV electrodes having a longest one of the RV-LV intrinsic conduction times. The LV pace/sense site may represent a site of latest LV activation within the multiple LV electrodes. The method may identify a site of latest LV activation to be utilized to determine the RV-LV conduction time and the LV-RV conduction time. During the LV only pacing mode, the IMD may be configured to not pace in the RV. The method may time delivery of RV and LV pacing pulses in the BiV pacing mode in a fusion timing manner with intrinsic conduction from the RA. The method may time delivery of pacing pulses in the LV only pacing mode in a fusion timing manner with intrinsic conduction from the RV apex along the LV.

DETAILED DESCRIPTION

Figure 1A:
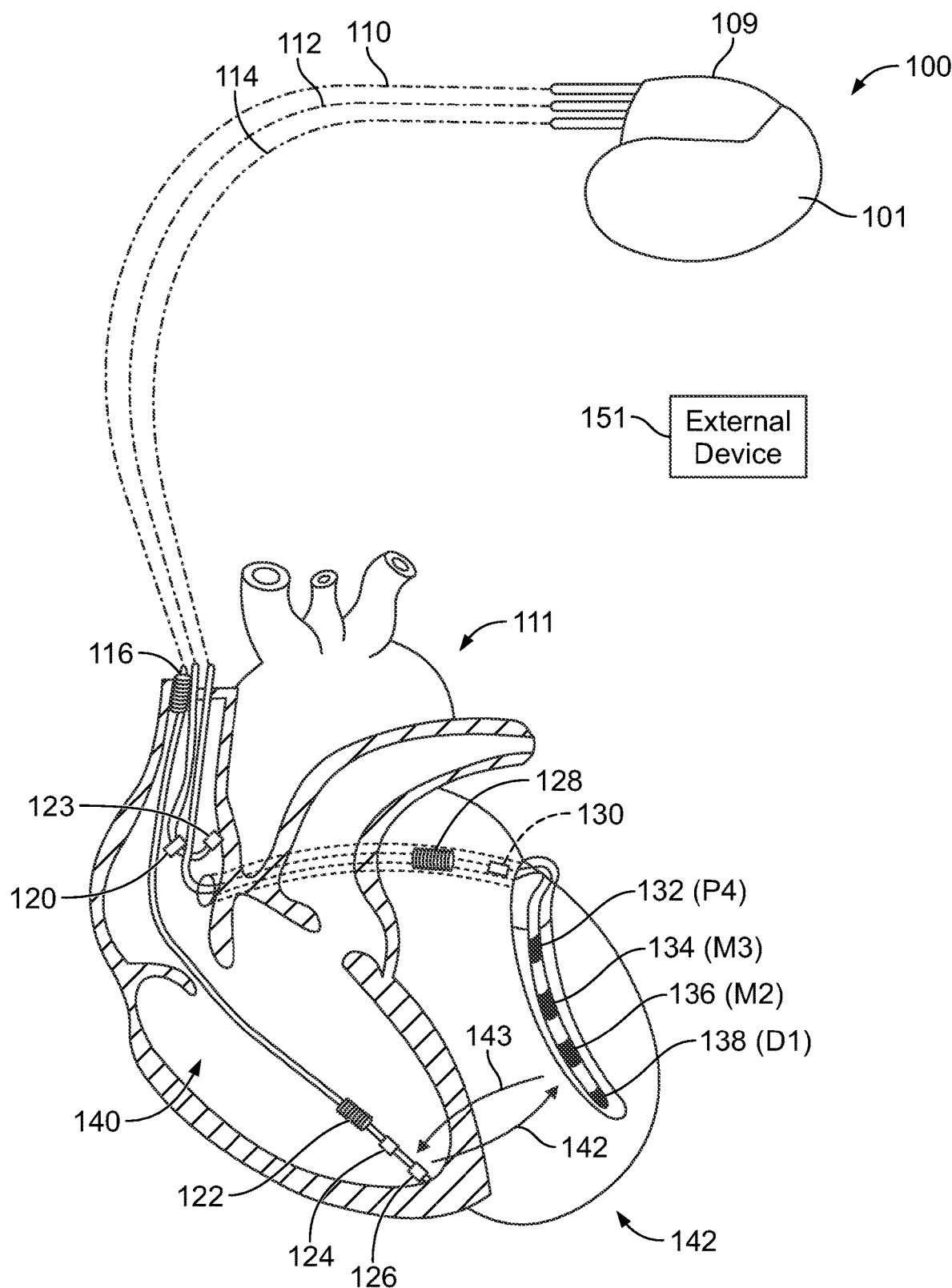
FIG. 1A illustrates an implantable medical device (IMD) intended for subcutaneous implantation at a site near the heart, in accordance with embodiments herein.

The abbreviations "RA", "LA", "RV" and "LV" refer to the right atrium, left atrium, right ventricle and the left ventricle respectively.

The abbreviations "RAp", "LAp", "RVp" and "LVp" refer to paced "p" events in the corresponding chamber, namely a right atrium paced event, left atrium paced event, right ventricle paced event and left ventricle paced event, respectively.

The abbreviations "RAs", "LAs", "RVs" and "LVs" refer to a sensed "s" events in the corresponding chamber, namely a right atrium sensed event, left atrium sensed event, right ventricle sensed event and left ventricle sensed event, respectively.

When a combination of any the foregoing abbreviations are provided separated by a dash "-" or slash "/", the combination indicated a characteristic of relation between the first paced/sensed event and the second sensed event. For example, the combination "RVp-LVs" refers to a paced event in the RV followed by a sensed event in the LV. Similarly, the combination of abbreviations "RAp-RVs" refers to a paced event in the RA followed by a sensed event in the RV. If the characteristic or relation is not otherwise indicated, the combination refers to a time interval (e.g., conduction time) between the correspond first and second events, such as a conduction time between an RA paced event (RAp) and a sensed LV event (LVs). Various combinations are discussed herein. When the chamber abbreviation (e.g., RV, LV) in a combination (e.g., (RV-LV, LV-RV) is not followed by a paced (p) or sensed (s) abbreviation, it is assumed that the first event is paced or sensed, and the second event is sensed.

The term "RV-LV conduction time" is used to refer to the conduction time between a first paced or sensed RV event and one or more subsequent responsive sensed LV events. For example, the sensed LV event may be at the LV sensing/pacing electrode designated as the LV pace/sense site of latest activation. As another example, the timing of the sensed LV event may be an average or other mathematical combination of when an evoked response is detected at multiple LV sensing/pacing electrodes.

The term "LV-RV conduction time" is used to refer to the conduction time between one or more first paced or sensed LV events and the subsequent sensed RV event.

The term "LVp-RVs conduction time" is used to refer to the conduction time between one or more paced events in the LV and a corresponding evoked response sensed in the RV.

The term "LVs-RVs conduction time" is used to refer to the conduction time between one or more sensed events in the LV and a corresponding evoked response sensed in the RV.

The term "RVp-LVs conduction time" is used to refer to the conduction time between a paced event in the RV and a corresponding one or more evoked responses sensed in the LV.

The term "RVs-LVs conduction time" is used to refer to the conduction time between a sensed event in the RV and a corresponding one or more evoked responses sensed in the LV.

The terms "VV conduction time difference" and "VV CT difference" refer to the difference between opposed interventricular conduction times, such as the difference between the RVp-LVs conduction time and the LVp-RVs conduction time, and/or the difference between the RVs-LVs conduction time and the LVs-RVs conduction time.

The terms "atrioventricular delay" and "AVD" refer to a programmed time delay to be used by the implantable medical device in connection with delivering therapy.

The term "intrinsic RV/LV interval" refers to measured intrinsic conduction time between an intrinsic event at an RV sensing site and a corresponding intrinsic event at an LV sensing site.

The terms "cardiac activity signal", "cardiac activity signals", "CA signal" and "CA signals" (collectively "CA signals") are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/arrhythmic. Non-limiting examples of CA signals include ECG signals collected by cutaneous electrodes, and EGM signals collected by subcutaneous electrodes and/or by electrodes positioned within or proximate to the heart wall and/or chambers of the heart.

The term "subcutaneous" shall mean below the skin, but not intravenous. For example, a subcutaneous electrode/lead does not include an electrode/lead located in a chamber of the heart, in a vein on the heart, or in the lateral or posterior branches of the coronary sinus.

The term "marker" refers to data and/or information identified from CA signals that may be presented as graphical and/or numeric indicia indicative of one or more features within the CA signals and/or indicative of one or more episodes exhibited by the cardiac events. Markers may be superimposed upon CA signals or presented proximate to, and temporally aligned with, CA signals. Non-limiting examples of markers may include R-wave markers, noise markers, activity markers, interval markers, refractory markers, P-wave markers, T-wave markers, PVC markers, sinus rhythm markers, atrial fibrillation (AF) markers and other arrhythmia markers. As a further non-limiting example, basic event markers may include "AF entry" to indicate a beginning of an AF event, "in AF" to indicate that AF is ongoing, "AF exit" to indicate that AF has terminated, "T" to indicate a tachycardia beat, "B" to indicate a bradycardia beat, "A" to indicate an asystole beat, "VS" to indicate a regular sinus beat, "Tachy" to indicate a tachycardia episode, "Brady" to indicate a Bradycardia episode, "Asystole" to indicate an asystole episode, "Patient activated" to indicate a patient activated episode. An activity marker may indicate activity detected by activity sensor during the CA signal. Noise markers may indicate entry/start, ongoing, recovery and exit/stop of noise. Markers may be presented as symbols, dashed lines, numeric values, thickened portions of a waveform, and the like. Markers may represent events, intervals, refractory periods, ICM activity, and other algorithm related activity. For example, interval markers, such as the R-R interval, may include a numeric value indicating the duration of the interval. The AF markers indicate atrial fibrillation rhythmic.

The term "device documented marker" refers to markers that are declared by an implantable cardiac monitor and/or implantable medical device. Any or all of the foregoing examples of markers represent device document markers. Markers may be declared based on numerous criteria, such as signal processing, feature detection and AF detection software and hardware within and/or operating on the implantable cardiac monitor and/or implantable medical device.

The term "COI" refers to a characteristic of interest within CA signals. Non-limiting examples of COI from a PQRST complex, include an R-wave, P-wave, T-wave and isoelectric segments. Non-limiting examples of COI from CA signals collected at an individual electrode(s) include a sensed event (e.g., an intrinsic event or evoked response). The COI may correspond to a peak of an individual sensed event, R-wave, an average or median P, R or T-wave peak and the like.

The term "LV only pacing" refers to a mode of operation for an implanted medical device in which the LV is paced, but the RV is not paced, when an intrinsic LV event is not detected before corresponding atrioventricular (AV) timer and/or interventricular (VV) timer timeout. The LV only pacing may be implemented utilizing a single LV electrode, which is referred to as LV single site or LV SS pacing. The LV pacing may also be implemented utilizing multiple LV electrodes, which is referred to as LV multipoint pacing or LV MPP. The LV pacing mode is maintained for a period of time, such as for 5 or more minutes, for a series of at least 5 heart beats/cycles and the like.

The terms "biventricular pacing" and "BiV pacing" refer to a mode of operation for an implantable medical device in which the LV and the RV are both paced, when intrinsic LV and RV events, respectively, are not detected before corresponding AV and/or VV timer timeout. The BiV pacing mode is maintained for a period of time, such as for 5 or more minutes, for a series of at least 5 heart beats/cycles and the like.

The term "real-time" refers to a time frame contemporaneous with normal or abnormal episode occurrences. For example, a real-time process or operation would occur during or immediately after (e.g., within minutes or seconds after) a cardiac event, a series of cardiac events, an arrhythmia episode, and the like.

The term "obtains" and "obtaining", as used in connection with data, signals, information and the like, include at least one of i) accessing memory of an external device or remote server where the data, signals, information, etc. are stored, ii) receiving the data, signals, information, etc. over a wireless communications link between the IMD and a local external device, and/or iii) receiving the data, signals, information, etc. at a remote server over a network connection. The obtaining operation, when from the perspective of an IMD, may include sensing new signals in real time, and/or accessing memory to read stored data, signals, information, etc. from memory within the IMD. The obtaining operation, when from the perspective of a local external device, includes receiving the data, signals, information, etc. at a transceiver of the local external device where the data, signals, information, etc. are transmitted from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

System Overview

In accordance with new and unique aspects herein, methods and systems are described that take advantage of device measured interventricular delays. The paced and sensed conduction time between RV and LV electrodes are recorded and used to select between BiV and LV only pacing. The LV only pacing may be LVSS pacing or LV MPP. In yet further embodiments, the paced and sensed relations between the conduction times between the RV and LV electrodes are recorded and used to select between BiV and LVSS pacing modes.

FIG. 1A illustrates an implantable medical device (IMD) 100 intended for subcutaneous implantation at a site near the heart 111, in accordance with embodiments herein. The IMD 100 is configured to wirelessly communicate with an external device 151. By way of example, the external device 151 may represent a physician's programmer, a smart phone, laptop computer, bedside monitoring station and the like. The IMD 100 may be a dual-chamber stimulation device, capable of treating both fast and slow arrhythmias with stimulation therapy, including cardioversion, pacing stimulation, an implantable cardioverter defibrillator, suspend tachycardia detection, tachyarrhythmia therapy, and/or the like. The IMD 100 may include a housing 101 to hold the electronic/computing components. The housing 101 (which is often referred to as the "can," "case," "encasing," or "case electrode") may be programmably selected to act as the return electrode for certain stimulus modes. The housing 101 further includes a connector 109 with a plurality of terminals 200-210 (shown in FIG. 2).

The IMD 100 is shown in electrical connection with a heart 111 by way of a left atrial (LA) lead 120 having a right lead 112 and a left atrial (LA) ring electrode 128. The IMD 100 is also in electrical connection with the heart 111 by way of a right ventricular (RV) lead 110 having, in this embodiment, a left ventricle (LV) electrode 132 (e.g., P4), an LV electrode 134 (e.g., M3), an LV electrode 136 (e.g., M2), and an LV electrode 138 (e.g., D1). The RV lead 110 is transvenously inserted into the heart 111 to place the RV coil 122 in the RV apex, and the SVC coil electrode 116. Accordingly, the RV lead 110 is capable of receiving cardiac signals and delivering stimulation in the form of pacing and shock therapy to the right ventricle 140 (also referred to as the RV chamber). The IMD 100 includes RV electrode 126, and a right atrium (RA) electrode 123. The RV lead 110 includes an RV tip electrode 126, an RV ring electrode 124, an RV coil electrode 122, and an SVC coil electrode 116.

The IMD 100 includes a left ventricle 142 (e.g., left chamber) pacing therapy, and is coupled to a multi-pole LV lead 114 designed for placement in various locations such as a "CS region" (e.g., venous vasculature of the left ventricle, including any portion of the coronary sinus (CS), great cardiac vein, left marginal vein, left posterior ventricular vein, middle cardiac vein, and/or small cardiac vein or any other cardiac vein accessible by the coronary sinus), the epicardial space, and/or the like.

In an embodiment, the LV lead 114 is designed to receive atrial and ventricular cardiac signals and to deliver left ventricular pacing therapy using a set of multiple LV electrodes 132, 134, 136, 138. The LV lead 114 also may deliver left atrial pacing therapy using at least an LA ring electrode 128 and shocking therapy using at least the LA ring electrode 128. In alternate embodiments, the LV lead 114 includes the LV electrodes 138, 136, 134, and 132, but does not include the LA electrode 130. The LV lead 114 may be, for example, the Quartet™ LV pacing lead developed by St. Jude Medical Inc. (headquartered in St. Paul, Minn.), which includes four pacing electrodes on the LV lead. Although three leads 110, 112, and 114 are shown in FIG. 1, fewer or additional leads with various configurations of pacing, sensing, and/or shocking electrodes may optionally be used. For example, the LV lead 114 may have more or less than four LV electrodes 132-138.

The LV electrode 132 (also referred to as P4) is shown as being the most "distal" LV electrode with reference to how far the electrode is from the right ventricle 140. The LV electrode 138 (also referred to as D1) is shown as being the most "proximal" LV electrode 132-138 to the left ventricle 142. The LV electrodes 136 and 134 are shown as being "middle" LV electrodes (also referred to as M3 and M2), between the distal and proximal LV electrodes 138 and 132, respectively. Accordingly, so as to more aptly describe their relative locations, the LV electrodes 138, 136, 134, and 132 may be referred to respectively as electrodes D1, M2, M3, and P4 (where "D" stands for "distal", "M" stands for "middle", and "P" stands from "proximal", and the s are arranged from most distal to most proximal, as shown in FIG. 1). Optionally, more or fewer LV electrodes may be provided on the lead 114 than the four LV electrodes D1, M2, M3, and P4.

The LV electrodes 132-138 are configured such that each electrode may be utilized to deliver pacing pulses and/or sense pacing pulses (e.g., monitor the response of the LV tissue to a pacing pulse). In a pacing vector or a sensing vector, each LV electrode 132-138 may be controlled to function as a cathode (negative electrode). Pacing pulses may be directionally provided between electrodes to define a pacing vector. In a pacing vector, a generated pulse is applied to the surrounding myocardial tissue through the cathode. The electrodes that define the pacing vectors may be electrodes in the heart 111 or located externally to the heart 111 (e.g., on a housing/case device 101). For example, the housing/case 101 may be referred to as the housing 101 and function as an anode in unipolar pacing and/or sensing vectors. The RV coil 122 may also function as an anode in unipolar pacing and/or sensing vectors. The LV electrodes 132-138 may be used to provide various different vectors. Some of the vectors are intraventricular LV vectors (e.g., vectors between two of the LV electrodes 132-138), while other vectors are interventricular vectors (e.g., vectors between an LV electrode 132-138 and an RV 122-126 or another electrode remote from the left ventricle 142). Optionally, various other types of leads may be used and the IMD 100 may be used with various other types of electrodes and combinations of electrodes. The foregoing electrode types/combinations are provided as non-limiting examples. Further, it is recognized that utilizing an RV coil electrode as an anode is merely one example. Various other electrodes may be configured as the anode electrode.

In accordance with embodiments herein, the IMD 100 chooses one of the electrodes 132-138 to be utilized in connection with measuring RV-LV and LV-RV conduction times. For example, the IMD 100 may choose the one of the electrodes 132-138 that exhibits the "latest activation" time following an intrinsic atrial event. For example, the IMD detect an RA intrinsic event and "listen", at each of the LV electrodes 132-138 for a corresponding intrinsic LV event. The LV electrodes 132-138 will detect the intrinsic LV event at different points in time and in different orders depending on the health condition of the surrounding heart tissue. For example, the IMD may determine that electrode 136 (M2) was the last LV electrode to sense an intrinsic event propagating along the LV. The IMD 100 selects the one of the electrodes 132-138 that sensed the latest activation time in connection with measuring subsequent RV-LV and LV-RV conduction times.

To measure the RV-LV conduction time, the IMD 100 delivers an RV paced event (e.g., electrode 126) and collects cardiac activity signals utilizing a sensing vector that includes the LV electrode associated with the latest activation time (e.g., electrode 136). For example, the sensing vector may extend between the electrode 136 and the housing 101, or alternatively between the electrode 136 and another LV electrode (e.g., 132). As another example, the sensing vector may extend between the electrode 136 and one or more RV electrodes (e.g., electrode 122). The IMD 100 and/or external device detects 151 the point in time at which an evoked response occurs at the LV electrode 136, where the evoked response is responsive to the RV paced event. The RV-LV conduction time 142 is the time interval measurement between the time at which the paced event was delivered and the time at which the evoked response was detected at the LV electrode. The RV-LV conduction time 142 may be determined the IMD 100 and/or an external device 151.

To measure the LV-RV conduction time, the IMD 100 delivers an LV paced event at the same LV electrode utilized when measuring the RV-LV conduction time (e.g., electrode 136). The IMD 100 collects cardiac activity signals at the RV electrode 126. The IMD 100 and/or external device 151 detects the point in time at which an evoked response occurs at the RV electrode (e.g., electrode 126) responsive to the LV paced event. The LV-RV conduction time 143 is the time measurement between the time at which the paced event was delivered and the evoked response was detected at the RV electrode. The LV-RV conduction time 143 may be determined by the IMD 100 and/or an external device 151.

The IMD 100 and/or external device 151 calculate a relation between the RV-LV and LV-RV conduction times and set a pacing mode of the IMD 100 to one of a BiV pacing mode and an LV only pacing mode. The LV only pacing mode may be set to the LVSS pacing mode or LV MPP mode. While the IMD 100 delivers paced events and collects CA signals, all or a portion of the processing of such signals (and the setting of the pacing mode) may be performed by the IMD 100 and/or external device 151.

Figure 1B:
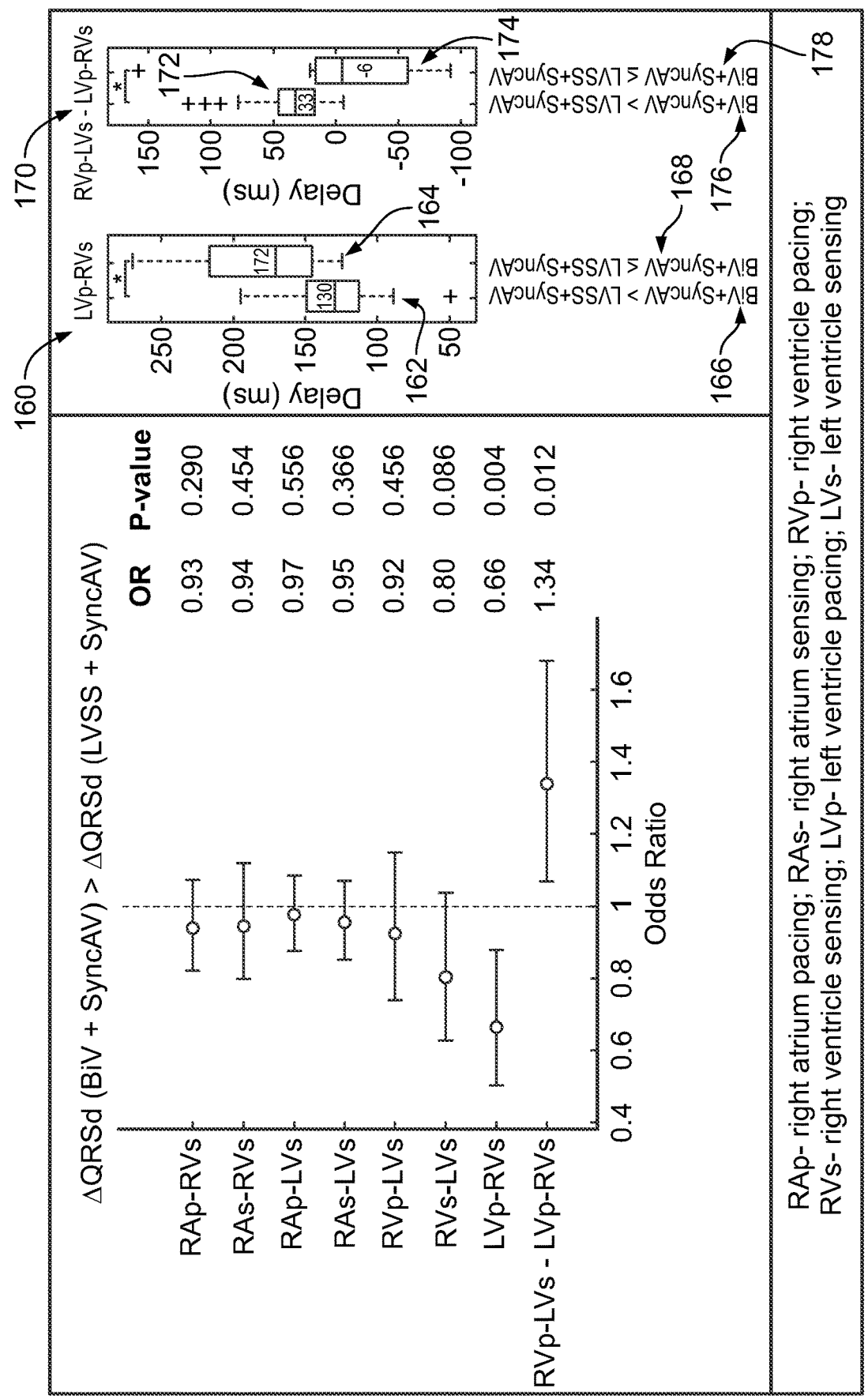
FIG. 1B illustrates examples modeling an extent to which various types of conduction times are predictive of improvement in hemodynamic performance in accordance with embodiments herein.

FIG. 1B illustrates examples modeling an extent to which various types of conduction times are predictive of improvement in hemodynamic performance. Hemodynamic performance is indicated by a duration of the QRS complex. An improvement in hemodynamic performance is indicated by a shortening or narrowing of the QRS complex, relative to a reference/intrinsic QRS complex.

It is believed that patients experience improved hemodynamics when patients exhibit a relatively narrow QRS complex. For example, a patient may exhibit one duration for an intrinsic QRS complex, representing the time duration between the beginning and end of the QRS complex, when no pacing therapy is delivered. For the same patient, a biventricular pacing therapy may be delivered and the duration of the biventricular paced QRS complex may be determined. Depending upon the nature of the patient's physiologic health and/or heart condition, biventricular pacing may result in a shorter/narrower QRS complex, as compared to the patient's intrinsic QRS complex when no therapy was delivered. As another alternative, the biventricular pacing may have little or no effect on the duration of the QRS complex, or even lengthen/widen the QRS complex relative to the intrinsic QRS complex, thereby indicating a potential negative impact on hemodynamic performance.

The same patient may then receive an LV single site or LV multipoint pacing therapy, for which a corresponding LV only paced QRS complex may be determined. Again, depending on the nature of the patient's physiologic health and/or heart condition, LV only pacing may result in a shorter/narrower QRS complex, as compared to the patient's intrinsic QRS complex when no therapy was delivered. As another alternative, the LV only pacing may have little or no effect on the duration of the QRS complex, or even lengthen/widen the QRS complex relative to the intrinsic QRS complex.

In accordance with new and unique aspects herein, it has been found that certain types of conduction times between corresponding regions of the heart are relatively strong predictors of whether biventricular pacing or LV only pacing is more likely to shorten/narrow the QRS complex, relative to the intrinsic QRS complex. In particular, a study was conducted for a number of patients. Intrinsic QRS complex durations were determined for the patient's while no therapy was delivered. Separately, the patients were treated with biventricular pacing, while corresponding QRS complex durations were measured. The patients were further treated (separately) utilizing LV single site only pacing, while further corresponding QRS complex durations were measured. A determination was made whether biventricular pacing or LV only pacing achieved a greater reduction in the patient's QRS complex relative to the patient's intrinsic QRS complex (e.g., an improvement in therapy-assisted hemodynamic performance relative to a patient's non-therapy intrinsic hemodynamic performance).

For each of the patients, various types of cardiac conduction times were also measured. The conduction times for the patient population were analyzed relative to which of the pacing modes achieved better reduction in the QRS complex duration. FIG. 1B presents the results from the analysis in the left and right panels. The left panel represents an "odds ratio" plot for a binomial regression analysis comparing the different types of conduction times as predictors for which of the pacing modes (biventricular or LV only) will produce a greater reduction in the QRS complex duration.

The left panel within FIG. 1B illustrates, along the left vertical axis, the different types of cardiac conduction times that were measured, namely the conduction time between: i) RAp-RVs, ii) RAs-RVs, iii) RAp-LVs, iv) RAs-LVs, v) RVp-LVs, vi) RVs-LVs, and vii) LVp-RVs. The bottom row of the left panel corresponds to a relation between two interventricular conduction times, name of the difference between the a) RVp-LVs, and the b) LVp-RVs.

The horizontal axis represents the "odds ratio" from the analysis, with a vertical dashed line at an odds value of 1. The odds ratio indicates a likelihood that an event will occur, expressed as a proportion, namely whether a particular conduction time is a strong or weak indicator of whether the QRS complex duration will be shortened by BiV pacing versus LV only pacing. The vertical dashed line, at OR=1, represents a point at which the corresponding conduction time has substantially no predictive value of the impact of the two pacing modes upon the intrinsic QRS complex duration. The OR values greater than one indicate an increased occurrence of a particular event (e.g., biventricular pacing achieves shorter QRS durations, as compared to LV only pacing). Hence, an OR value greater than 1, for a corresponding conduction time, would indicate that biventricular pacing may be preferred for a particular patient. The OR values less than 1 indicate a decreased occurrence of a particular event (e.g., biventricular pacing achieves shorter QRS durations, as compared to LV only pacing). Hence, an OR value less than 1, for a corresponding conduction time, would indicate that LV only pacing may be preferred for a particular patient.

FIG. 1B also plots P values in connection with each conduction time. The P value represents a statistical probability of obtaining a particular result, which in the present example, is whether biventricular pacing achieves a greater reduction in the QRS complex duration, as compared to LV only pacing. The RAp-RVs conduction time has an OR value of 0.93 and a P value of 0.290, and thus represents a very poor predictor of which pacing mode is more likely to reduce a patient's QRS complex duration. The RVs-LVs conduction time has an OR value of 0.80 and a P value of 0.086, and is thus a slightly better predictor, as compared to the RAp-RVs conduction time, of which pacing mode may be more effective. The remaining paced and sensed conduction times from the RA do not afford better predictors. The RAs-RVs and RAs-LVs conduction times between intrinsic RA, RV and LV events have ORs of 0.94 and 0.95, respectively, and P values of 0.454 and 0.366, respectively. Thus, when taken alone, the RAs-RVs and RAs-LVs conduction times for intrinsic events between the RA, RV and LV also do not exhibit very strong predictors of which pacing mode (BiV or LV only) is better suited to reduce the patient's QRS complex duration.

FIG. 1B illustrates 3 interventricular (VV) conduction times and one mathematical relation (difference) between two VV conduction times, all of which appear to afford slightly better predictive results than the RA-based conduction times. However, the intrinsic VV conduction time (RVs-LVs) does not afford a very strong predictor.

In accordance with new and unique aspects herein, it has been found that, the best 2 predictors represent the LVp-RVs conduction time and the interventricular conduction time difference (e.g., RVp-LVs and LVp-RVs conduction times, collectively referred to as the VV CT difference). Interestingly, the RVp-LVs conduction time, when taken alone, does not appear to afford a very strong predictive value, having an OR of 0.92 and a P value of 0.456. Yet, the conduction time in the opposite direction, namely the LVp-RVs conduction time, is a good predictor having an OR of 0.66 and a P value of 0.004, which is substantially better than the first (top) six conduction times i) RAp-RVs, ii) RAs-RVs, iii) RAp-LVs, iv) RAs-LVs, v) RVp-LVs, and vi) RVs-LVs. Even more interesting, when the two opposed VV conduction times are mathematically combined, the relation there between affords the best predictor. More specifically, the VV conduction time difference, namely RVp-LVs minus LVp-RVs, has an OR of 1.34 and a P value of 0.012, which is also substantially better than the first six conduction times i) RAp-RVs, ii) RAs-RVs, iii) RAp-LVs, iv) RAs-LVs, v) RVp-LVs, and vi) RVs-LVs.

The foregoing analysis illustrates that not all types of conduction times yield similar information when attempting to predict which pacing mode is best for a particular patient. The foregoing analysis illustrates the unexpected result that only certain VV conduction times and certain mathematical combinations of conduction times afford the best predictors of a preferred pacing mode to use for a particular patient. Also, not all interventricular conduction times are equally predictive. The intrinsic VV conduction time (RVs-LVs) and the RVp-LVs conduction time are not as strong of predictors as the LVp-RVs and the VV CT difference.

Next, in accordance with new and unique aspects herein, it is determined how to apply thresholds relative to the conduction time based predictors. The right panel in FIG. 1B illustrates a statistical combination of the conduction times exhibited by the patient population. The plot 160 concerns the LVp-RVs conduction times of the patient population. The plot 170 concerns the VV CT difference exhibited by the patient population.

The plot 160 is presented as first and second candlesticks 162, 164, corresponding to respective first and second groups 166, 168 within the patient population. The first group 166 represents patients who experienced a greater reduction in the QRS complex duration in response to biventricular pacing, as compared to their QRS complex durations when treated with LV only pacing. The first group 166 exhibited a mean LVp-RVs conduction time of 130 ms with outliers at approximately 75 ms and 190 ms. The second group 168 represents patients who experienced a greater reduction in the QRS complex duration in response to LV only pacing (single site), as compared to their QRS complex durations when treated with biventricular pacing. The second group 168 exhibited a mean LVp-RVs conduction time of 172 ms with outliers at approximately 120 ms and 270 ms.

The plots 162, 164 further indicate that patients who have LVp-RVs conduction times less than or equal to 150 ms, or more preferably less than or equal to 140 ms, or even more preferably between 80 ms and 150 ms, are more likely to experience a greater reduction in QRS complex duration when treated with biventricular therapy, as compared to LV only pacing.

The plot 170 concerns the VV CT differences of the patient population, separated into first and second groups 176, 178. The plot is separated into first and second candlesticks 172, 174 corresponding to respective first and second groups 176, 180 of the patient population. The first group 176 represents patients who experienced a greater reduction in the QRS complex duration in response to biventricular pacing, as compared to their QRS complex durations when treated with LV only pacing. The first group 176 exhibited a mean VV CT difference of 33 ms with outliers at −5 ms and 80 ms. The second portion 178 represents patients who experienced a greater reduction in the QRS complex duration in response to LV only pacing (single site), as compared to their QRS complex durations when treated with biventricular pacing. The second group 178 exhibited a mean VV DC difference of −6 ms with outliers at approximately −95 ms and 25 ms. The plot 170 indicates that patients, who respond better to biventricular pacing, exhibit slower conduction from the RV to the LV, as compared to the conduction rate from the LV to the RV. The plot 170 further indicates that patients, who respond better to LV only pacing, exhibit faster conduction from the RV to the LV, as compared to the conduction rate from the LV to the RV.

The plots 172, 174 further indicate that patients who have VV CT difference greater than 0 ms, more preferably greater than 20 ms, and even more preferably between 10 ms and 100 ms, are more likely to experience a greater reduction in QRS complex duration when treated with biventricular therapy, as compared to LV only pacing. The foregoing unexpected results are utilized to develop new and unique methods and systems as described herein.

Figure 2:
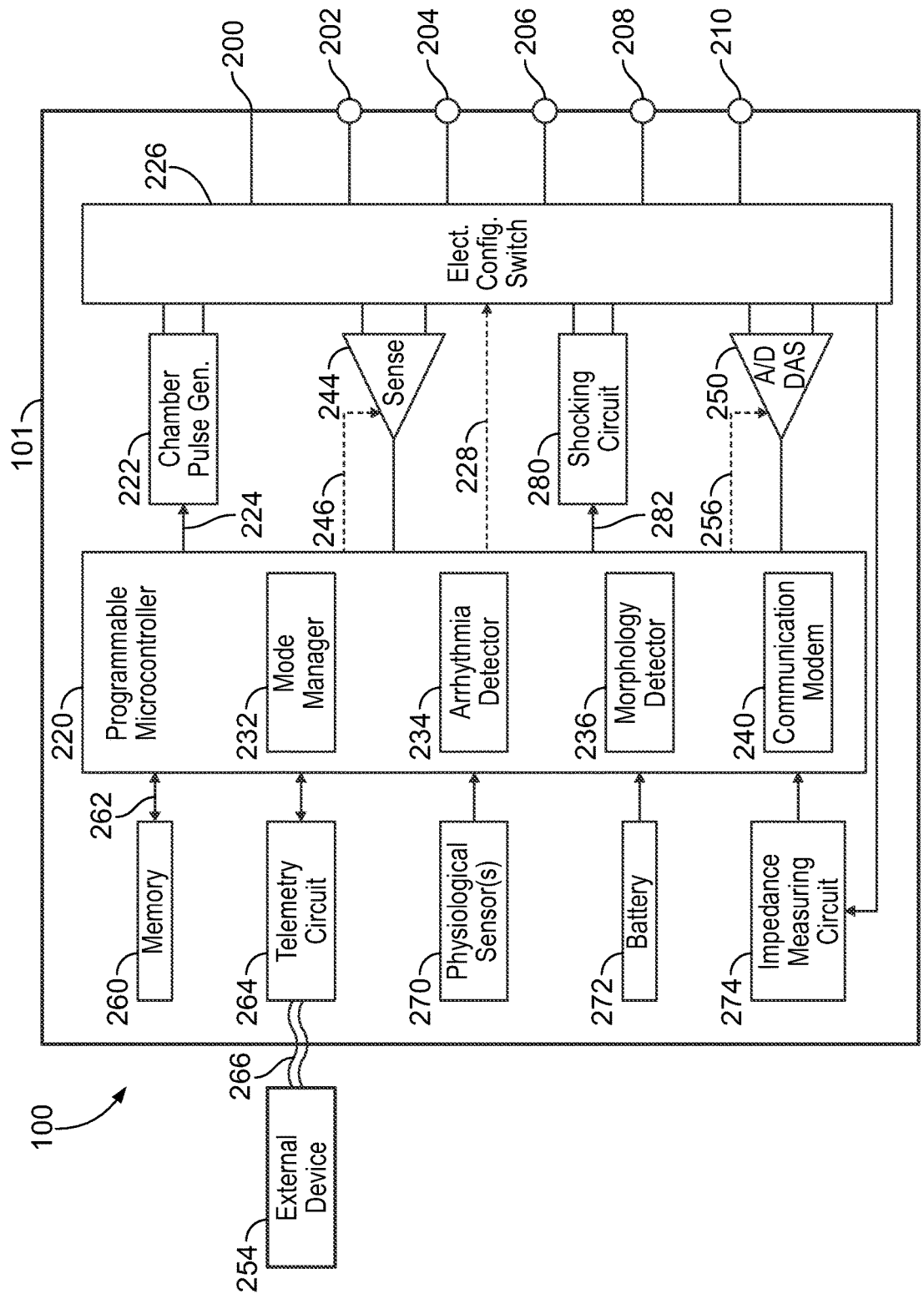
FIG. 2 illustrates a schematic view of the IMD in accordance with embodiments herein.

FIG. 2 illustrates a schematic view of the IMD 100. The IMD 100 may be a dual-chamber stimulation device, capable of treating both fast and slow arrhythmias with stimulation therapy, including cardioversion, pacing stimulation, an implantable cardioverter defibrillator, suspend tachycardia detection, tachyarrhythmia therapy, and/or the like.

The IMD 100 has a housing 101 to hold the electronic/computing components. The housing 101 (which is often referred to as the "can," "case," "encasing," or new to me makes "case electrode") may be programmably selected to act as the return electrode for certain stimulus modes. The housing 101 further includes a connector (not shown) with a plurality of terminals 200-210. The terminals may be connected to electrodes that are located in various locations within and around the heart. For example, the terminals may include: a terminal 200 to be coupled to a first electrode (e.g., a tip electrode) located in a first chamber; a terminal 202 to be coupled to a second electrode located in a second chamber; a terminal 204 to be coupled to an electrode located in the first chamber; a terminal 206 to be coupled to an electrode located in the second chamber; an a terminal 208 to be coupled to an electrode; and a terminal 210 to be coupled to an electrode located in the shocking circuit 280. The type and location of each electrode may vary. For example, the electrodes may include various combinations of a ring, a tip, a coil and shocking electrodes and the like.

The IMD 100 includes a programmable microcontroller 220 that controls various operations of the IMD 100, including cardiac monitoring and stimulation therapy. The microcontroller 220 is also referred to throughout, and in the claims, as one or more processors or at least one processor. The microcontroller 220 includes a microprocessor (or equivalent control circuitry), RAM and/or ROM memory, logic and timing circuitry, state machine circuitry, and I/O circuitry. The IMD 100 further includes an atrial and/or ventricular pulse generator 222 that generates stimulation pulses for connecting the desired electrodes to the appropriate I/O circuits, thereby facilitating electrode programmability. The switch 226 is controlled by a control signal 228 from the microcontroller 220.

A pulse generator 222 is illustrated in FIG. 2. Optionally, the IMD 100 may include multiple pulse generators, similar to the pulse generator 222, where each pulse generator is coupled to one or more electrodes and controlled by the microcontroller 220 to deliver select stimulus pulse(s) to the corresponding one or more electrodes. The IMD 100 includes sensing circuitry 244 selectively coupled to one or more electrodes that perform sensing operations, through the switch 226 to detect the presence of cardiac activity in the chamber of the heart 111. The output of the sensing circuitry 244 is connected to the microcontroller 220 which, in turn, triggers, or inhibits the pulse generator 222 in response to the absence or presence of cardiac activity. The sensing circuitry 244 receives a control signal 246 from the microcontroller 220 for purposes of controlling the gain, threshold, polarization charge removal circuitry (not shown), and the timing of any blocking circuitry (not shown) coupled to the inputs of the sensing circuitry.

In the example of FIG. 2, the sensing circuit 244 is illustrated. Optionally, the IMD 100 may include multiple sensing circuits 244, similar to the sensing circuit 244, where each sensing circuit is coupled to one or more electrodes and controlled by the microcontroller 220 to sense electrical activity detected at the corresponding one or more electrodes. The sensing circuit 224 may operate in a unipolar sensing configuration or a bipolar sensing configuration.

The IMD 100 further includes an analog-to-digital (ND) data acquisition system (DAS) 250 coupled to one or more electrodes via the switch 226 to sample cardiac signals across any pair of desired electrodes. The ND converter 250 is configured to acquire intracardiac electrogram signals, convert the raw analog data into digital data and store the digital data for later processing and/or telemetric transmission to an external device 254 (e.g., a programmer, local transceiver, or a diagnostic system analyzer). The ND converter 250 is controlled by a control signal 256 from the microcontroller 220.

The microcontroller 220 includes an arrhythmia detector 234 for analyzing cardiac activity signals sensed by the sensing circuit 244 and/or the ND converter 250. The arrhythmia detector 234 is configured to analyze cardiac signals sensed at various sensing sites. The arrhythmia detector 234 declares an arrhythmia, in response to which, the microcontroller 220 determines an appropriate therapy. For example, responsive to the arrhythmia detector 234 identifying a bradycardia arrhythmia, the microcontroller 220 directs the pulse generator 222 to deliver a pacing therapy.

The microcontroller 220 includes a mode manager 232 configured to executes program instructions to implement the operations described herein, such as determine a RV-LV conduction time representative of a conduction time between a right ventricular paced event and one or more responsive left ventricular sensed events. The mode manager 232 is further configured to determine at least one of: i) a right ventricular to left ventricular (RV-LV) conduction time representative of a conduction time between a right ventricular (RV) paced or sensed event and one or more responsive left ventricular (LV) sensed events; or ii) a left ventricular to right ventricular (LV-RV) conduction time representative of a conduction time between one or more LV paced or sensed events and an RV sensed event. The mode manager 232 is further configured to calculate a relation between a threshold and the at least one of the RV-LV conduction time or LV-RV conduction time. The mode manager 232 is further configured to set a pacing mode of the IMD 100 to one of i) a biventricular pacing mode and ii) an LV only pacing mode based on the relation between the RV-LV conduction time and the LV-RV conduction time.

Additionally or alternatively, an external device may determine at least one of: i) a right ventricular to left ventricular (RV-LV) conduction time representative of a conduction time between a right ventricular (RV) paced or sensed event and one or more responsive left ventricular (LV) sensed events; or ii) a left ventricular to right ventricular (LV-RV) conduction time representative of a conduction time between one or more LV paced or sensed events and an RV sensed event. The external device may further calculate a relation between a threshold and the at least one of the RV-LV conduction time or LV-RV conduction time. The external device may further determine the operating mode to be utilized by the IMD and convey an instruction to the IMD directing the IMD to set the operations therein to one of the BiV pacing mode or LV only pacing mode.

The mode manager 232 and/or external device may be further configured to, when calculating the relation, compare the threshold to at least one of i) the RV-LV conduction time, ii) the LV-RV conduction time, or iii) a difference between the RV-LV and LV-RV conduction times; and, when setting the pacing mode, to perform at least one of: i) set the pacing mode to the BiV pacing mode when the difference exceeds the threshold and to set the pacing mode to the LV only pacing mode when the difference equals or is below the threshold; ii) set the pacing mode to the BiV pacing mode when the RV-LV conduction time is below the threshold and to set the pacing mode to the LV only pacing mode when the difference equals or exceeds the threshold; or iii) set the pacing mode to the BiV pacing mode when the LV-RV conduction time is below the threshold and to set the pacing mode to the LV only pacing mode when the difference equals or exceeds the threshold.

The mode manager 232 and/or external device may be further configured to determine both of the RV-LV conduction time and the LV-RV conduction time and calculate, as the relation, a mathematical relation between the RV-LV conduction time and the LV-RV conduction time, the pacing mode set based on the mathematical relation.

Additionally or alternatively, the RV-LV conduction time may represent the conduction time between an RV paced event and an LV sensed event (RVp-LVs), the LV-RV conduction time may represent the conduction time between an LV paced event and an RV sensed event (LVp-RVs), and the relation may represent a difference between the RVp-LVs conduction time and the LVp-RVs conduction time.

The mode manager 232 and/or external device may be further configured to calculate, as the relation, a mathematical relation between the RV-LV conduction time and the LV-RV conduction time, the pacing mode set based on the mathematical relation. As explained herein, the mathematical relation may represent a difference between the RV-LV conduction time and the LV-RV conduction time. Additionally or alternatively, the mode manager 232 and/or external device may be further configured to compare the difference to a threshold and to set the pacing mode to the BiV pacing mode when the difference is below the threshold and to set the pacing mode to the LV only pacing mode when the difference equals or exceeds the threshold.

Optionally, embodiments herein may be implemented in connection with a single LV electrode, or in combination with multiple LV electrodes (e.g., as illustrated in FIG. 1).

When multiple LV electrodes are utilized, the mode manager 232 and/or external device may be further configured to identify one of the LV sites to utilize for pacing and sensing. For example, an LV site of latest LV activation may be utilized to determine the RV-LV conduction time and the LV-RV conduction time. For example, the mode manager 232 and/or external device may be further configured to measure intrinsic RV/LV intervals between an RV intrinsic event, measured at the RV electrode, and LV intrinsic events, measured at the corresponding LV electrodes. Based on the measured intrinsic RV/LV intervals, the mode manager 232 and/or external device select one of the LV electrodes as an LV pace/sense site to use to determine at least one of the RV-LV conduction time and/or the LV-RV conduction time. The LV pace/sense site selected will generally represent the one of the LV electrodes having a longest one of the RV-LV intrinsic conduction times. The LV pace/sense site represents a site of latest LV activation within the multiple LV electrodes. Optionally, the site of latest LV activation may be set based on intrinsic RA/LV intervals to each of the LV sensing sites.

During the LV only pacing mode, the microcontroller 220 is configured to not pace in the RV. The microcontroller 220 is further configured to time delivery of pacing pulses in the BiV pacing mode in a fusion timing manner with intrinsic conduction in at least one of the RV and LV. The microcontroller 220 is further configured to time delivery of pacing pulses in the LV only pacing mode in a fusion timing manner with intrinsic conduction from the RV apex along the LV. In accordance with embodiments herein, the pacing therapy is BiV pacing or LV only pacing. The microcontroller 220 may be further configured to time delivery of RV and LV pacing pulses in the BiV pacing mode in a fusion timing manner with intrinsic conduction from the RA.

The microcontroller 220 controls the timing of the stimulation pulses, the timing of refractory periods, blanking intervals, noise detection windows, evoked response windows, alert intervals, marker channel timing, and/or the like. The microcontroller 220 is operably coupled to a memory 260 by a suitable data/address bus 262. The programmable operating parameters used by the microcontroller 220 are stored in the memory 260 and used to customize the operation of the IMD 100 to suit the needs of a particular patient. The operating parameters of the IMD 100 may be non-invasively programmed into the memory 260 through a telemetry circuit 264 in telemetric communication via communication link 266 (e.g., MICS, Bluetooth low energy, and/or the like) with the external device 254.

The IMD 100 can further include one or more physiological sensors 270. Such sensors are commonly referred to as "rate-responsive" sensors because they are typically used to adjust pacing stimulation rates according to the exercise state of the patient. However, the physiological sensor 156 may further be used to detect changes in cardiac output, changes in the physiological condition of the heart, or diurnal changes in activity (e.g., detecting sleep and wake states). Signals generated by the physiological sensors 270 are passed to the microcontroller 220 for analysis. While shown as being included within the IMD 100, the physiological sensor(s) 270 may be external to the IMD 100, yet still, be implanted within or carried by the patient. Examples of physiological sensors might include sensors that, for example, sense respiration rate, pH of blood, ventricular gradient, activity, position/posture, minute ventilation (MV), and/or the like.

A battery 272 provides operating power to all of the components in the IMD 100. The battery 272 is capable of operating at low current drains for long periods of time, and is capable of providing a high-current pulses (for capacitor charging) when the patient requires a shock pulse (e.g., in excess of 2 A, at voltages above 2 V, for periods of 10 seconds or more). The battery 272 also desirably has a predictable discharge characteristic so that elective replacement time can be detected. As one example, the IMD 100 employs lithium/silver vanadium oxide batteries.

The IMD 100 further includes an impedance measuring circuit 274, which can be used for many things, including sensing respiration phase. The impedance measuring circuit 274 is coupled to the switch 226 so that any desired electrode and/or terminal may be used to measure impedance in connection with monitoring respiration phase. The microcontroller 220 further controls a shocking circuit 280 by way of a control signal 282. The shocking circuit 280 generates shocking pulses of low (e.g., up to 0.5 joules), moderate (e.g., 0.5-10 joules), or high energy (e.g., 11 to 40 joules), as controlled by the microcontroller 220. Such shocking pulses are applied to the patient's heart through shocking electrodes. Maybe noted that the shock therapy circuitry is optional and may not be implemented in the IMD 100.

The microcontroller 220 further includes a timing control used to control the timing of stimulation pulses (e.g., pacing rate, atria-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and the like. The AV delay is managed to provide a fusion AV delay to fuse timing of pacing pulses with intrinsic wave fronts. The timing control may also control VV delays such as in connection a delay management process referred to as "SyncAV", as further described in the patents and publications incorporated hereby reference. The timing control may also be used for the timing of refractory periods, blanking intervals, noise detection windows, evoked response windows, alert intervals, marker channel timing, and so on. Microcontroller 220 also has a morphology detector 236 to review and analyze one or more features of the morphology of cardiac signals. Although not shown, the microcontroller 220 may further include other dedicated circuitry and/or firmware/software components that assist in monitoring various conditions of the patient's heart and managing pacing therapies.

The switch 226 includes a plurality of switches for connecting the desired electrodes to the appropriate I/O circuits, thereby providing complete electrode programmability. Accordingly, the switch 226, in response to a control signal 228 from the microcontroller 220, determines the polarity of the stimulation pulses (e.g., unipolar, bipolar, etc.) by selectively closing the appropriate combination of switches (not shown) as is known in the art.

The IMD 100 is further equipped with a communication modem (modulator/demodulator) 240 to enable wireless communication with other devices, implanted devices and/or external devices. In one implementation, the communication modem 240 may use high-frequency modulation of a signal transmitted between a pair of electrodes. As one example, the signals may be transmitted in a high-frequency range of approximately 10-80 kHz, as such signals travel through the body tissue and fluids without stimulating the heart or being felt by the patient.

Figure 3A:
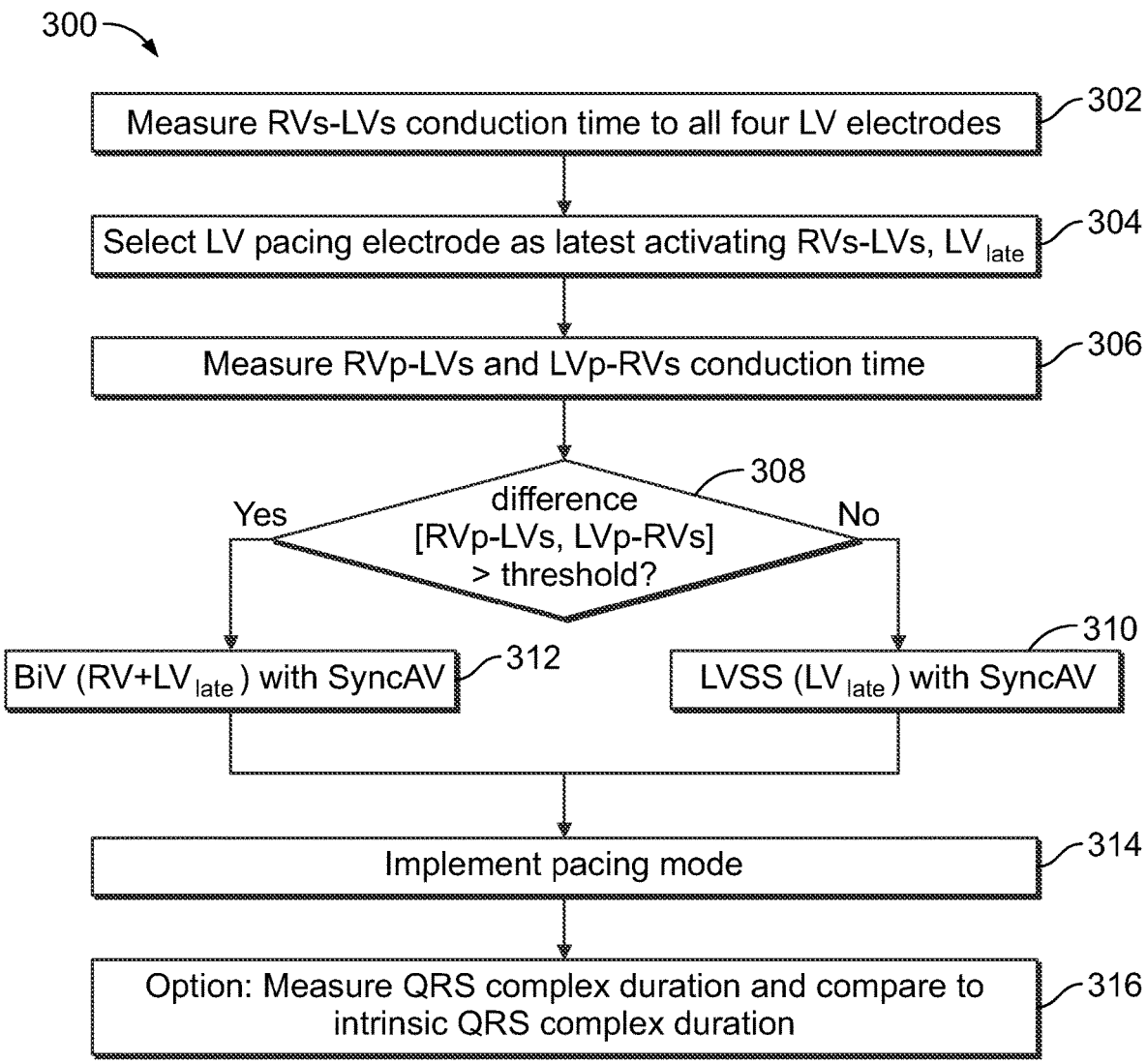
FIG. 3A illustrates a computer implemented method for discriminating between BiV pacing and LV only pacing modes, in accordance with embodiments herein.

FIG. 3A illustrates a computer implemented method 300 for discriminating between biventricular (BiV) pacing and left ventricular (LV) only pacing modes, in accordance with embodiments herein. The method 300 may be under control of one or more processors configured with specific executable instructions. The one or more processors may be implemented partially or entirely within the IMD, partially or entirely within an external device, partially or entirely within a bedside monitoring station, remote server and the like.

Figure 4B:
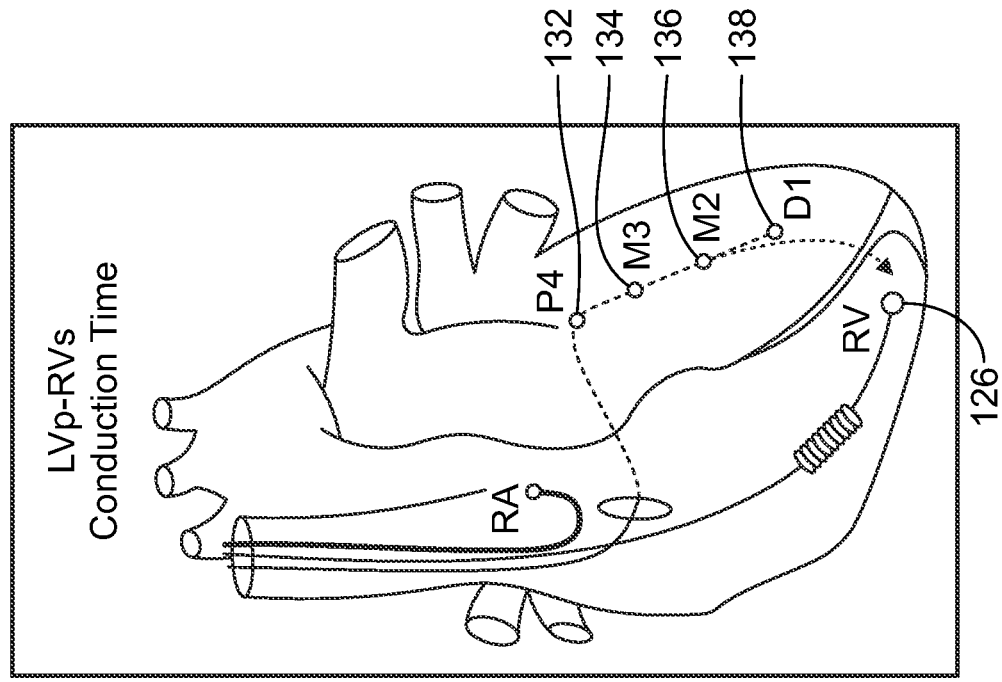
FIG. 4B illustrates examples of conduction times between one or more LV electrodes and an RV electrode in accordance with embodiments herein.
Figure 4A:
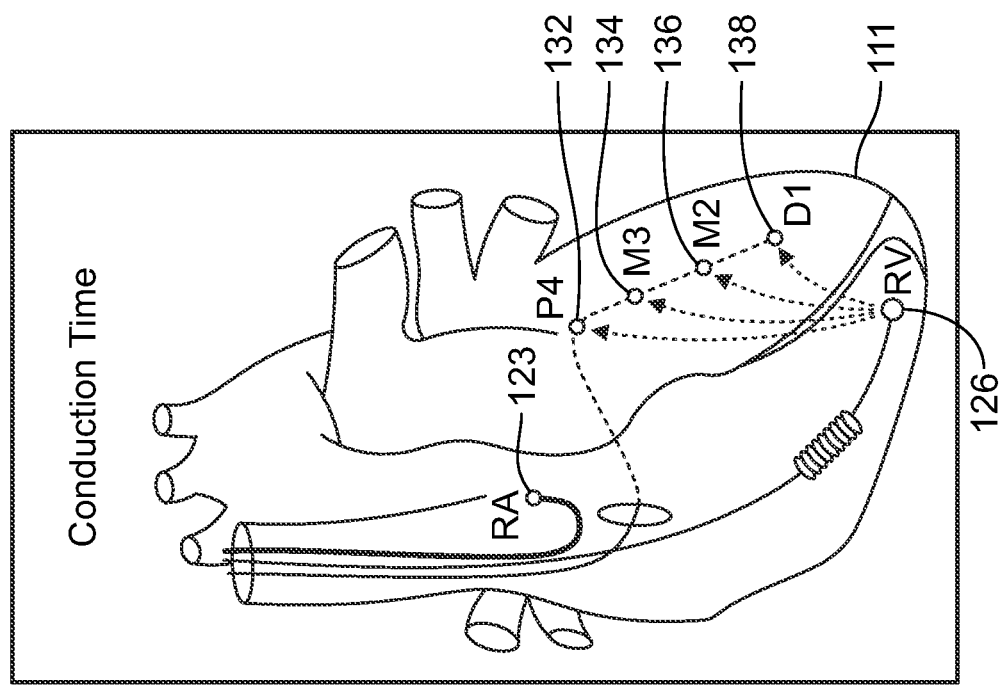
FIG. 4A illustrates examples of conduction times between an RV electrode and one or more LV electrodes in accordance with embodiments herein.

At 302, the one or more processors measure an intrinsic RVs-LVs conduction time associated with each of the LV sensing sites. For example, in connection with FIG. 4, the one or more processors measure the conduction time between an intrinsic event detected at the RV electrode 126 and each of the LV electrodes 132-138. The one or more processors may utilize the sensed event at the RV electrode 126 to start one or more timers. The timers identify the conduction time at which a propagating wave progresses across the LV until sensed by the LV electrodes 132-138 (e.g., the peak of the propagating wave).

At 304, the one or more processors compare the conduction times for the intrinsic RV-LV intervals at the LV electrodes 132-138 relative to each other to identify the intrinsic RV-LV interval that has a desired characteristic (e.g., the latest LV site to detect the propagating wave). For example, the one or more processors identify the longest conduction time between the RV electrode 126 and one of the LV electrodes 132-138. The latest LV conduction site $LV_{late}$ is designated/selected as the LV pacing/since site to be utilized for pacing and sensing. The LV pace/sense site selected represents the one of the LV electrodes having a longest one of the RV-LV intrinsic conduction times. The one or more processors set the configuration mode of the IMD to utilize the designated/selected one of the LV electrodes. The LV pace/sense site represents a site of latest LV activation within the multiple LV electrodes.

The operation at 304 is utilized when it is desirable to afford an LV only pacing mode that utilizes a single LV site for pacing. Alternatively, in some instances it may be desirable to utilize LV MPP as the LV only pacing mode. When LV MPP is utilized, an individual LV electrode need not be selected, and optionally the operation at 304 may be omitted. Additionally or alternatively, the operation at 304 may be implemented, but a further selection is made between LV single site pacing and LV MPP.

At 306, the one or more processors determine a conduction time between an RV paced event and the corresponding LV sensed event. The LV sensed event may be detected at the LV pace/sense site designated as the site of latest LV activation within the multiple LV electrodes. For example, in connection with FIG. 4A, the one or more processors measure the conduction time between the RV paced event at the RV electrode 126 and the selected one of the LV electrodes, such as LV electrode 136. The one or more processors initiate a timer when a paced event occurs at the RV electrode 126. The timer is stopped when the propagating wave is sensed at LV electrode 136. The one or more processors identify the RVp-LVs conduction time based on the timer.

Optionally, the RVp-LVs conduction time may be calculated as the conduction time between an RV paced event and a combination of the timing of evoked responses sensed at multiple LV electrodes (e.g., 132-136, 132-138, 134 and 138, etc.). For example, the timing of the sensed LV event may be an average or other mathematical combination of when an evoked response is detected at multiple LV sensing/pacing electrodes.

At 306, the one or more processors also determine a conduction time between an LV paced event and the corresponding RV sensed event. For example, in connection with FIG. 4B, the one or more processors measure the conduction time between the LV paced event at the selected one of the LV electrodes (e.g., LV electrode 136) and the RV electrode 126. The one or more processors initiate a timer when a paced event occurs at the LV electrode 136. The timer is stopped when the propagating wave is sensed at RV electrode 126. The one or more processors identify the LVp-RVs conduction time based on the timer. Optionally the determinations of the RV-LV conduction time and LV-RV conduction time may be performed by one or more processors of an external device and/or remote server based on remote review of CA signals wirelessly transmitted from the IMD.

At 308, the one or more processors calculate a relation between a threshold and the RV-LV conduction time and the LV-RV conduction time. For example, the calculation may include calculating, as the relation, a mathematical relation between the RVp-LVs conduction time and the LVp-RVs conduction time. As explained above, in accordance with embodiments herein, it has been found that one preferred mathematical relation represents a difference between the RVp-LVs conduction time and the LVp-RVs conduction time, namely the VV CT difference.

As explained above, it has been found that, at least 2 preferred predictors represent the LVp-RVs conduction time and the interventricular conduction time difference (e.g., the VV CT difference).

At 308, when calculating the relation, the one or more processors compare the threshold to the VV CT difference between the RV-LV and LV-RV conduction times. Based on the comparison, flow branches between 310 and 312 to set a pacing mode of the IMD to the select one of i) a biventricular (BiV) pacing mode and ii) an LV only pacing mode based on the relation between the RV-LV conduction time and the LV-RV conduction time.

When the VV CT difference is equal to or below the threshold, flow branches to 310. At 310, the pacing mode is set to an LV only pacing mode with SyncAV. In the present example, the pacing mode is set to the LV SS pacing mode with SyncAV, utilizing the LV site of latest activation $LV_{late}$. During the LV only pacing mode, the IMD is configured to not pace in the RV. The IMD will continue to provide LV only pacing until the pacing mode is changed, which may not occur for a relatively extended period of time but at least not for several minutes or several beats. The SyncAV function is applied such that the LV only pacing is timed to deliver pacing pulses in the LV only pacing mode in a fusion timing manner with intrinsic conduction from the RV apex along the LV.

When the VV CT difference is above the threshold, flow branches to 312. At 312, the pacing mode is set to the BiV pacing mode. In the present example, the BiV pacing mode also utilizes the LV site of latest activation $LV_{late}$. During the BiV pacing mode, the IMD is configured to pace in the RV and in the LV. The IMD will continue to provide Rv and LV pacing until the pacing mode is changed, which may not occur for a relatively extended period of time but at least not for several minutes or several beats. Optionally, the BiV pacing may be configured to time RV and LV pacing pulses in the BiV pacing mode in a fusion timing manner with intrinsic conduction from the RA.

At 314, once the pacing mode is set at 310 or 312, the IMD utilizes the corresponding pacing mode until it is determined to change the pacing mode. Once set, a pacing mode will continue for at least several minutes or several heartbeats before being changed.

Optionally, a confirmation process may be implanted at 316. For example, at 316, the one or more processors may collect additional measurements of the QRS complex duration associated with the new pacing mode (set at 310 or 312). The QRS complex duration may be measured for one or a series of successive beats. Optionally, the QRS complex duration may be measured periodically over a predetermined period of time. The QRS complex durations may then be combined in various mathematical forms (e.g., mean, average, median). The one or more processors may then compare the QRS complex duration, associated with the new pacing mode, to the initial intrinsic QRS complex duration that was collected when no pacing therapy was delivered.

As a further option, the QRS complex duration, associated with the new pacing mode, may be compared to a previously collected QRS complex duration associated with the other pacing mode. For example, when it is determined at 310 to set the current pacing mode to the LV single site only pacing mode, a related QRS complex duration may be collected over time at 316 and compared to a previously obtained QRS complex duration that was collected while the IMD was operating in a BiV pacing mode. Based on the comparisons of the QRS complex durations, the one or more processors may determine that the pacing mode implemented at 314 is achieving a desired improvement by narrowing the QRS complex duration (e.g., relative to the intrinsic QRS complex duration and/or relative to the other pacing mode QRS complex duration). Alternatively, the one or more processors may determine that the pacing mode implemented at 314 is not achieving a desired improvement, but instead is resulting in worse hemodynamic performance (e.g., by lengthening the QRS complex duration). Various responses may be implemented, such as to reverting to a base pacing mode, switching to the other one of the BiV pacing mode or LV only pacing mode and the like.

Optionally, the process of FIG. 3A may be implemented in connection with a relation (e.g., difference) between an RVs-LVs conduction time and an LVs-RVs conduction time. For example, at 326, the one or more processors measure RVs-LVs and LVs-RVs conduction times. At 328 a difference is determined between an RVs-LVs conduction time and an LVs-RVs conduction time (e.g., the VV CT difference. The VV CT difference is compared to a threshold. Based on the comparison, flow branches between 310 and 312 to set a pacing mode of the IMD to the select one of i) a biventricular (BiV) pacing mode and ii) an LV only pacing mode based on the relation between the RV-LV conduction time and the LV-RV conduction time. When the VV CT difference is equal to or below the threshold, flow branches to 310. When the VV CT difference is above the threshold, flow branches to 312.

Optionally, the process of FIG. 3A may be implemented in connection with a relation (e.g., difference) between an RVp-LVs conduction time and an LVs-RVs conduction time. Optionally, the process of FIG. 3A may be implemented in connection with a relation (e.g., difference) between an RVs-LVs conduction time and an LVp-RVs conduction time. When the VV CT difference is equal to or below the threshold, flow branches to 310. When the VV CT difference is above the threshold, flow branches to 312.

The foregoing embodiments are described in connection with RV and LV sensing/pacing sites. Additionally or alternatively, embodiments may utilize a pacing/sensing electrode located at the HIS bundle and/or at the left bundle branch (LBB). For example, a Hp-RVs conduction time may be measured between an HIS bundle paced event and a corresponding evoked response (RV sensed event). Similarly, a Hp-LVs conduction time may be measured between an HIS bundle paced event and one or more corresponding evoked responses (LV sensed event(s)). The relation may represent a VV CT difference corresponding to the difference between the Hp-RVs conduction time and the Hp-LVs conduction time. The relation is then compared to a threshold and flow branches to 310 or 312 based on the comparison. For example, when the VV CT difference is equal to or below the threshold, flow branches to 310. When the VV CT difference is above the threshold, flow branches to 312.

Additionally or alternatively, Hs-RVs and Hs-LVs conduction times may be measured and used to calculate the relation. The relation is then compared to a threshold and flow branches to 310 or 312 based on the comparison. For example, when the VV CT difference is equal to or below the threshold, flow branches to 310. When the VV CT difference is above the threshold, flow branches to 312.

For example a method and system may be provided that comprises: at least one implantable lead comprising a HIS bundle (H) electrode, a right ventricular (RV) electrode and one or more left ventricular (LV) electrodes; at least one processor; and a memory coupled to the at least one processor, wherein the memory stores program instructions, wherein the program instructions are executable by the at least one processor to: determine at least one of: i) a HIS paced or sensed to right ventricular (Hp-RVs) or (Hs-RVs) conduction time or ii) a HIS paced or sensed to left ventricular (Hp-LVs) or (Hs-LVs) conduction time. The process or one or more processors calculate a relation between a threshold and the at least one of the Hp-RVs, Hs-RVs, Hp-LVs or Hs-LVs conduction time and set a pacing mode of an implantable medical device to one of i) a biventricular (BiV) pacing mode and ii) an LV only pacing mode based on the relation.

Additionally or alternatively, a LBB-RVs conduction time may be measured between an LBB paced event and a corresponding evoked response (RV sensed event). Similarly, a LBBp-LVs conduction time may be measured between an LBB paced event and one or more corresponding evoked responses (LV sensed event(s)). The relation may represent a VV CT difference corresponding to the difference between the LBBp-RVs conduction time and the LBBp-LVs conduction time. The relation is then compared to a threshold and flow branches to 310 or 312 based on the comparison. For example, when the VV CT difference is equal to or below the threshold, flow branches to 310. When the VV CT difference is above the threshold, flow branches to 312.

Additionally or alternatively, LBBs-RVs and LBBs-LVs conduction times may be measured and used to calculate the relation. The relation is then compared to a threshold and flow branches to 310 or 312 based on the comparison. For example, when the VV CT difference is equal to or below the threshold, flow branches to 310. When the VV CT difference is above the threshold, flow branches to 312.

For example a method and system may be provided that comprises: at least one implantable lead comprising a LBB electrode, a right ventricular (RV) electrode and one or more left ventricular (LV) electrodes; at least one processor; and a memory coupled to the at least one processor, wherein the memory stores program instructions, wherein the program instructions are executable by the at least one processor to: determine at least one of: i) a LBB paced or sensed to right ventricular (LBBp-RVs) or (LBBs-RVs) conduction time or ii) a LBB paced or sensed to left ventricular (LBBp-LVs) or (LBBs-LVs) conduction time. The process or one or more processors calculate a relation between a threshold and the at least one of the LBBp-RVs, LBBs-RVs, LBBp-LVs or LBBs-LVs conduction time and set a pacing mode of an implantable medical device to one of i) a biventricular (BiV) pacing mode and ii) an LV only pacing mode based on the relation.

Figure 3B:
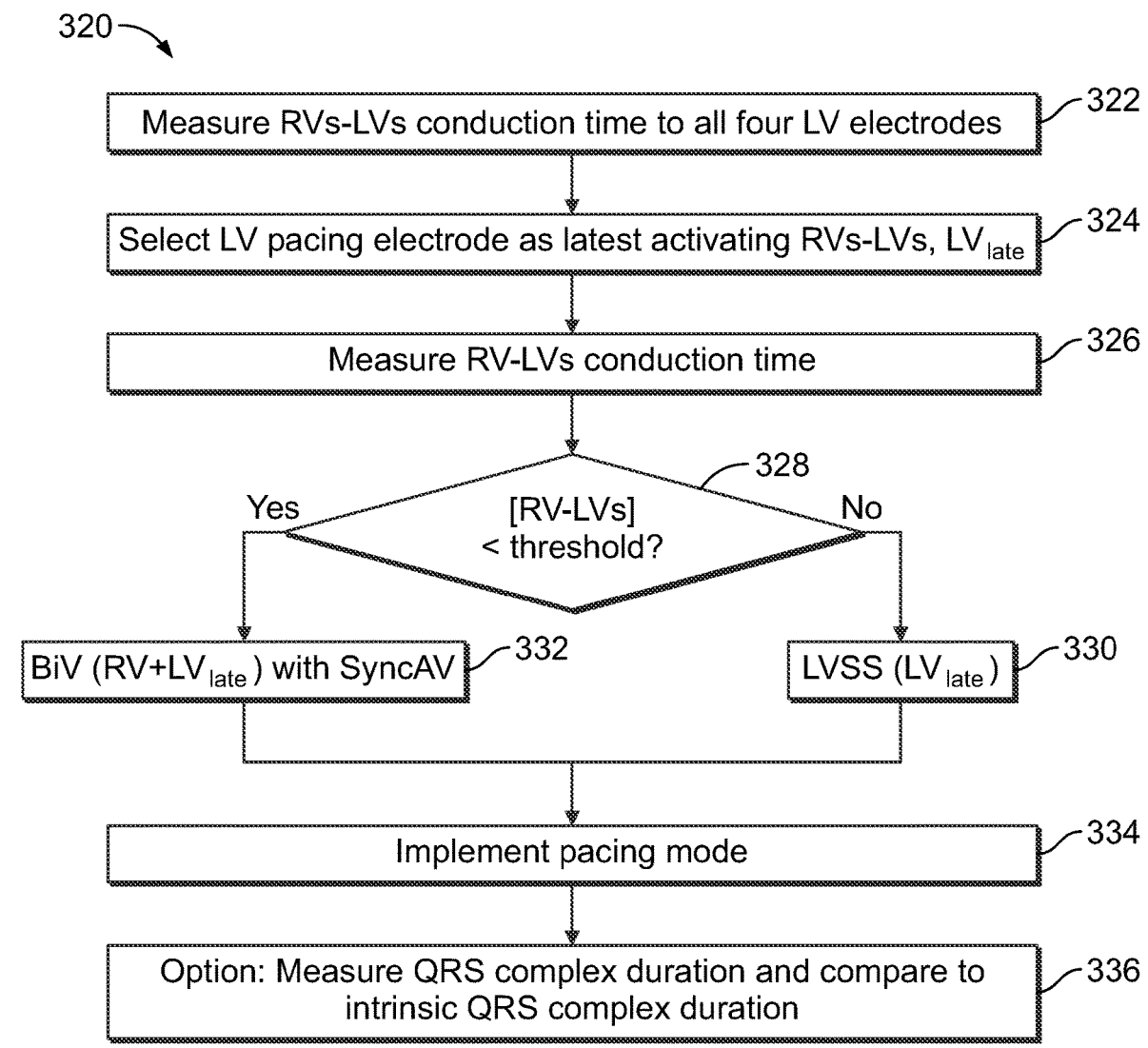
FIG. 3B illustrates a computer implemented method for discriminating between BiV pacing and LV only pacing modes, in accordance with alternative embodiments herein.

FIG. 3B illustrates a computer implemented method 320 for discriminating between biventricular (BiV) pacing and left ventricular (LV) only pacing modes, in accordance with alternative embodiments herein. At 322, the one or more processors measure an intrinsic RVs-LVs conduction time associated with each of the LV sensing sites. At 324, the one or more processors compare the conduction times for the intrinsic RV-LV intervals at the LV electrodes 132-138 relative to each other to identify the intrinsic RV-LV interval that has a desired characteristic (e.g., the latest LV site to detect the propagating wave). For example, the one or more processors identify the longest conduction time between the RV electrode 126 and one of the LV electrodes 132-138. The latest LV conduction site $LV_{late}$ is designated/selected as the LV pacing/since site to be utilized for pacing and sensing. The LV pace/sense site selected represents the one of the LV electrodes having a longest one of the RV-LV intrinsic conduction times. The one or more processors set the configuration mode of the IMD to utilize the designated/selected one of the LV electrodes. The LV pace/sense site represents a site of latest LV activation within the multiple LV electrodes.

The operation at 324 is utilized when it is desirable to afford an LV only pacing mode that utilizes a single LV site for pacing. Alternatively, in some instances it may be desirable to utilize LV MPP as the LV only pacing mode. When LV MPP is utilized, an individual LV electrode need not be selected, and optionally the operation at 324 may be omitted. Additionally or alternatively, the operation at 324 may be implemented, but a further selection is made between LV single site pacing and LV MPP.

At 326, the one or more processors determine a conduction time between an RV sensed event and the corresponding LV sensed event. At 328, the one or more processors calculate a relation between the RVs-LVs conduction time and a threshold. For example, the relation may be a comparison of the RVs-LVs conduction time to a threshold. Based on the comparison, flow branches between 330 and 332 to set a pacing mode of the IMD to the select one of i) a biventricular (BiV) pacing mode and ii) an LV only pacing mode based on the relation between the RVs-LVs conduction time and the threshold. When the RVs-LVs conduction time is equal to or greater than the threshold, flow branches to 330. At 330, the pacing mode is set to an LV only pacing mode with SyncAV. In the present example, the pacing mode is set to the LV SS pacing mode with SyncAV, utilizing the LV site of latest activation $LV_{late}$. During the LV only pacing mode, the IMD is configured to not pace in the RV. The IMD will continue to provide LV only pacing until the pacing mode is changed, which may not occur for a relatively extended period of time but at least not for several minutes or several beats.

When the RVs-LVs conduction time is below the threshold, flow branches to 332. At 332, the pacing mode is set to the BiV pacing mode. In the present example, the BiV pacing mode also utilizes the LV site of latest activation $LV_{late}$. During the BiV pacing mode, the IMD is configured to pace in the RV and in the LV. The IMD will continue to provide Rv and LV pacing until the pacing mode is changed, which may not occur for a relatively extended period of time but at least not for several minutes or several beats. Optionally, the BiV pacing may be configured to time RV and LV pacing pulses in the BiV pacing mode in a fusion timing manner with intrinsic conduction from the RA.

At 334, once the pacing mode is set at 330 or 332, the IMD utilizes the corresponding pacing mode until it is determined to change the pacing mode. Once set, a pacing mode will continue for at least several minutes or several heartbeats before being changed.

Optionally, a confirmation process may be implanted at 336. For example, at 336, the one or more processors may collect additional measurements of the QRS complex duration associated with the new pacing mode. The QRS complex duration may be measured for one or a series of successive beats. Optionally, the QRS complex duration may be measured periodically over a predetermined period of time. The QRS complex durations may then be combined in various mathematical forms (e.g., mean, average, median). The one or more processors may then compare the QRS complex duration, associated with the new pacing mode, to the initial intrinsic QRS complex duration that was collected when no pacing therapy was delivered.

As a further option, the QRS complex duration, associated with the new pacing mode, may be compared to a previously collected QRS complex duration associated with the other pacing mode. For example, when it is determined to set the current pacing mode to the LV single site only pacing mode, a related QRS complex duration may be collected over time at 336 and compared to a previously obtained QRS complex duration that was collected while the IMD was operating in a BiV pacing mode. Based on the comparisons of the QRS complex durations, the one or more processors may determine that the pacing mode implemented at 334 is achieving a desired improvement by narrowing the QRS complex duration (e.g., relative to the intrinsic QRS complex duration and/or relative to the other pacing mode QRS complex duration). Alternatively, the one or more processors may determine that the pacing mode implemented at 334 is not achieving a desired improvement, but instead is resulting in worse hemodynamic performance (e.g., by lengthening the QRS complex duration). Various responses may be implemented, such as to reverting to a base pacing mode, switching to the other one of the BiV pacing mode or LV only pacing mode and the like.

Figure 3C:
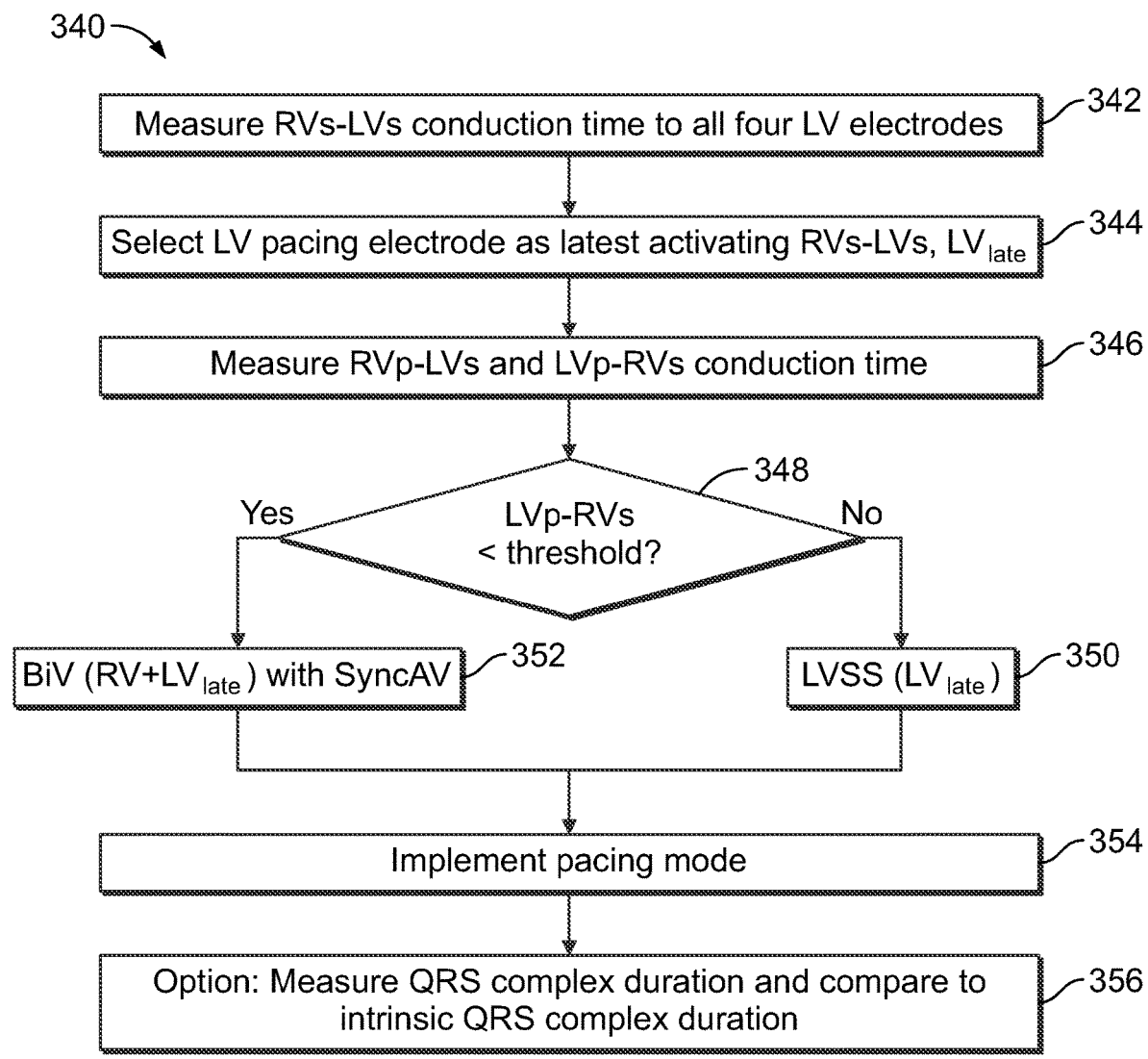
FIG. 3C illustrates a computer implemented method for discriminating between BiV pacing and LV only pacing modes, in accordance with alternative embodiments herein.

FIG. 3C illustrates a computer implemented method 340 for discriminating between biventricular (BiV) pacing and left ventricular (LV) only pacing modes, in accordance with alternative embodiments herein. At 342, the one or more processors measure an intrinsic RVs-LVs conduction time associated with each of the LV sensing sites. At 344, the one or more processors compare the conduction times for the intrinsic RV-LV intervals at the LV electrodes 132-138 relative to each other to identify the intrinsic RV-LV interval that has a desired characteristic (e.g., the latest LV site to detect the propagating wave). For example, the one or more processors identify the longest conduction time between the RV electrode 126 and one of the LV electrodes 132-138. The latest LV conduction site $LV_{late}$ is designated/selected as the LV pacing/since site to be utilized for pacing and sensing. The LV pace/sense site selected represents the one of the LV electrodes having a longest one of the RV-LV intrinsic conduction times. The one or more processors set the configuration mode of the IMD to utilize the designated/selected one of the LV electrodes. The LV pace/sense site represents a site of latest LV activation within the multiple LV electrodes.

The operation at 344 is utilized when it is desirable to afford an LV only pacing mode that utilizes a single LV site for pacing. Alternatively, in some instances it may be desirable to utilize LV MPP as the LV only pacing mode. When LV MPP is utilized, an individual LV electrode need not be selected, and optionally the operation at 344 may be omitted. Additionally or alternatively, the operation at 344 may be implemented, but a further selection is made between LV single site pacing and LV MPP.

At 346, the one or more processors determine a conduction time between an LVp paced event and the corresponding RV sensed event. At 348, the one or more processors calculate a relation between the LVp-RVs conduction time and a threshold. For example, the relation may be a comparison of the LVp-RVs conduction time to a threshold. Based on the comparison, flow branches between 350 and 352 to set a pacing mode of the IMD to the select one of i) a biventricular (BiV) pacing mode and ii) an LV only pacing mode based on the relation between the LVp-RVs conduction time and the threshold. When the LVp-RVs conduction time is equal to or greater than the threshold, flow branches to 350. At 350, the pacing mode is set to an LV only pacing mode with SyncAV. In the present example, the pacing mode is set to the LV SS pacing mode with SyncAV, utilizing the LV site of latest activation $LV_{late}$. During the LV only pacing mode, the IMD is configured to not pace in the RV. The IMD will continue to provide LV only pacing until the pacing mode is changed, which may not occur for a relatively extended period of time but at least not for several minutes or several beats.

When the LVp-RVs conduction time is below the threshold, flow branches to 352. At 352, the pacing mode is set to the BiV pacing mode. In the present example, the BiV pacing mode also utilizes the LV site of latest activation $LV_{late}$. During the BiV pacing mode, the IMD is configured to pace in the RV and in the LV. The IMD will continue to provide Rv and LV pacing until the pacing mode is changed, which may not occur for a relatively extended period of time but at least not for several minutes or several beats. Optionally, the BiV pacing may be configured to time RV and LV pacing pulses in the BiV pacing mode in a fusion timing manner with intrinsic conduction from the RA.

At 354, once the pacing mode is set at 350 or 352, the IMD utilizes the corresponding pacing mode until it is determined to change the pacing mode. Once set, a pacing mode will continue for at least several minutes or several heartbeats before being changed.

Optionally, a confirmation process may be implanted at 356. For example, at 356, the one or more processors may collect additional measurements of the QRS complex duration associated with the new pacing mode. The QRS complex duration may be measured for one or a series of successive beats. Optionally, the QRS complex duration may be measured periodically over a predetermined period of time. The QRS complex durations may then be combined in various mathematical forms (e.g., mean, average, median). The one or more processors may then compare the QRS complex duration, associated with the new pacing mode, to the initial intrinsic QRS complex duration that was collected when no pacing therapy was delivered.

As a further option, the QRS complex duration, associated with the new pacing mode, may be compared to a previously collected QRS complex duration associated with the other pacing mode. For example, when it is determined to set the current pacing mode to the LV single site only pacing mode, a related QRS complex duration may be collected over time at 356 and compared to a previously obtained QRS complex duration that was collected while the IMD was operating in a BiV pacing mode. Based on the comparisons of the QRS complex durations, the one or more processors may determine that the pacing mode implemented at 354 is achieving a desired improvement by narrowing the QRS complex duration (e.g., relative to the intrinsic QRS complex duration and/or relative to the other pacing mode QRS complex duration). Alternatively, the one or more processors may determine that the pacing mode implemented at 354 is not achieving a desired improvement, but instead is resulting in worse hemodynamic performance (e.g., by lengthening the QRS complex duration). Various responses may be implemented, such as to reverting to a base pacing mode, switching to the other one of the BiV pacing mode or LV only pacing mode and the like.

Optionally, the operations of FIGS. 3A-3C may be combined in various combinations and permutations. For example, when calculating the relation, the method and system may compare the threshold to any two or all of i) the RV-LV conduction time, ii) the LV-RV conduction time, and/or iii) a difference between the RV-LV and LV-RV conduction times. The method and system, when setting the pacing mode, may perform any two or all of: i) setting the pacing mode to the BiV pacing mode when the difference exceeds the threshold and to set the pacing mode to the LV only pacing mode when the difference equals or is below the threshold; ii) setting the pacing mode to the BiV pacing mode when the RV-LV conduction time is below the threshold and to set the pacing mode to the LV only pacing mode when the difference equals or exceeds the threshold; or iii) setting the pacing mode to the BiV pacing mode when the LV-RV conduction time is below the threshold and to set the pacing mode to the LV only pacing mode when the difference equals or exceeds the threshold.

Figure 5:
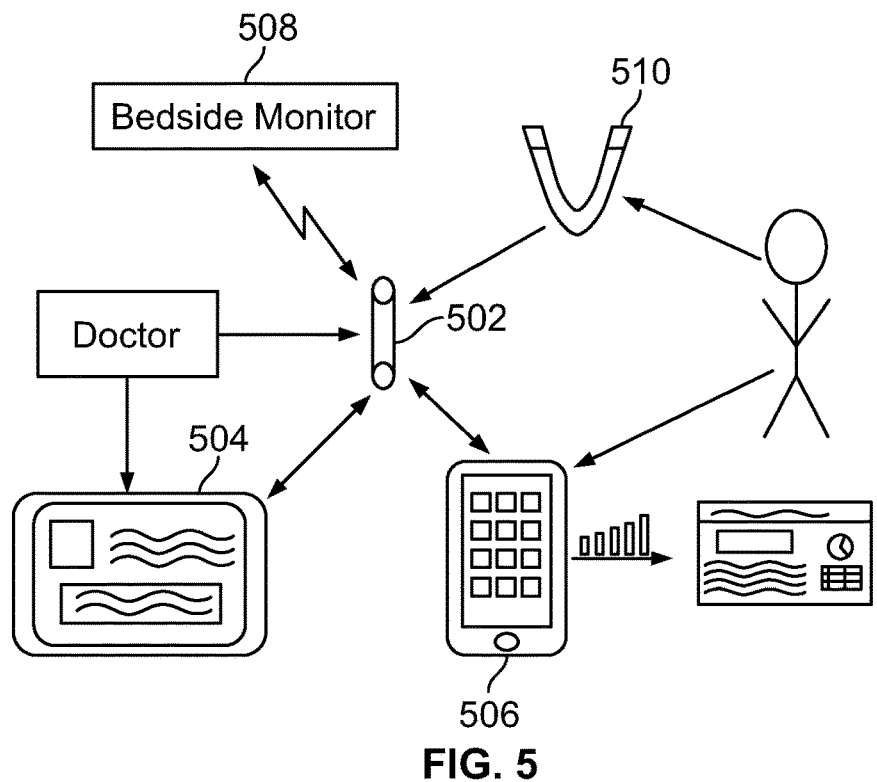
FIG. 5 illustrates a system level diagram indicating potential devices and networks that utilize the methods and systems herein.

FIG. 5 illustrates a system level diagram indicating potential devices and networks that utilize the methods and systems herein. For example, an implantable cardiac monitoring device (ICM) 502 may be utilized to collect a cardiac activity data set. The ICM 502 may supply the CA data set (CA signals and DD feature markers) to various local external devices, such as a tablet device 504, a smart phone 506, a bedside monitoring device 508, a smart watch and the like. The devices 504-508 include a display to present the various types of CA signals, markers, statistics, diagnostics and other information described herein. The ICM 502 may convey the CA data set over various types of wireless communications links to the devices 504, 506 and 508. The ICM 502 may utilize various communications protocols and be activated in various manners, such as through a Bluetooth, Bluetooth low energy, WiFi or other wireless protocol. Additionally or alternatively, when a magnetic device 510 is held next to the patient, the magnetic field from the device 510 may activate the ICM 502 to transmit the cardiac activity data set and AF data to one or more of the devices 504-508.

The processes described herein for analyzing the cardiac activity data, determining intrinsic RV-LV intervals, determining RV-LV conduction times, determining LV-RV conduction times, the determining VV CT differences and setting pacing modes may be implemented on one or more of the devices 504-508. Additionally or alternatively, the ICM 502 may also implement the confirmatory processes. The devices 504-508 may present the CA data set, measured intervals and conduction times, along with the determined mode settings, to clinicians in various manners. Additionally or alternatively, the duration and heart rate under AF may be formatted into histograms or other types of charts to be presented alone or in combination with CA signals. Additionally or alternatively, the devices 504-508 may further measure initial QRS complex durations and later QRS complex durations (e.g., following a setting to a BiV pacing mode and/or following a setting to a LV only pacing mode). The devices 504-508 may then present, to the clinician, the raw QRS complex durations and/or various measurements and statistical analysis of the QRS complex durations.

Figure 6:
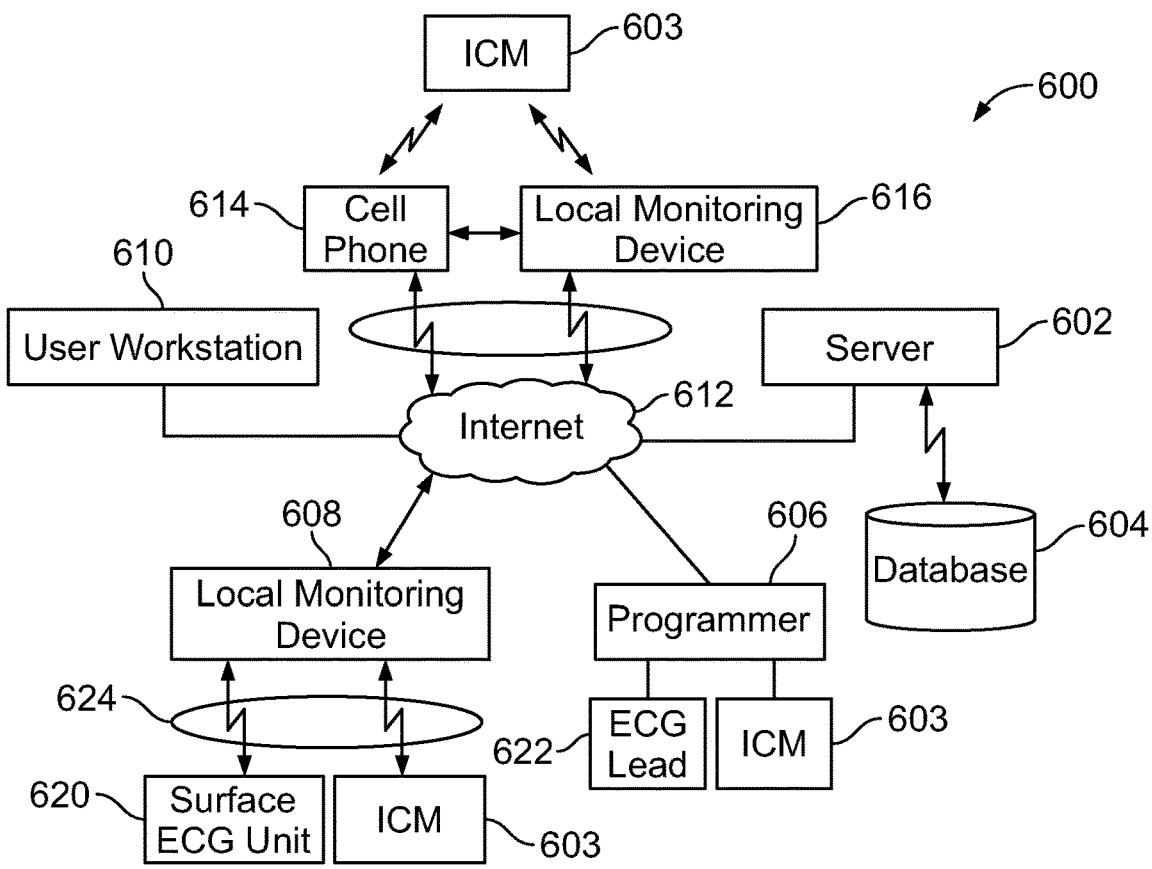
FIG. 6 illustrates a distributed processing system in accordance with embodiments herein.

FIG. 6 illustrates a distributed processing system 600 in accordance with embodiments herein. The distributed processing system 600 includes a server 602 connected to a database 604, a programmer 606, a local monitoring device 608 and a user workstation 610 electrically connected to a network 612. Any of the processor-based components in FIG. 6 (e.g., workstation 610, cell phone 614, local monitoring device 616, server 602, programmer 606) may perform the processes discussed herein.

The network 612 may provide cloud-based services over the internet, a voice over IP (VoIP) gateway, a local plain old telephone service (POTS), a public switched telephone network (PSTN), a cellular phone based network, and the like. Alternatively, the communication system may be a local area network (LAN), a medical campus area network (CAN), a metropolitan area network (MAN), or a wide area network (WAM). The communication system serves to provide a network that facilitates the transfer/receipt of data and other information between local and remote devices (relative to a patient). The server 602 is a computer system that provides services to the other computing devices on the network 612. The server 602 controls the communication of information such as cardiac activity data sets, bradycardia episode information, asystole episode information, AF episode information, markers, cardiac signal waveforms, heart rates, and device settings. The server 602 interfaces with the network 612 to transfer information between the programmer 606, local monitoring devices 608, 616, user workstation 610, cell phone 614 and database 604. The database 604 stores information such as cardiac activity data, QRS complex durations, RV-LV conduction times, LV-RV conduction times, VV CT differences, AF episode information, AF statistics, diagnostics, markers, cardiac signal waveforms, heart rates, device settings, and the like, for a patient population. The information is downloaded into the database 604 via the server 602 or, alternatively, the information is uploaded to the server 602 from the database 604. The programmer 606 may reside in a patient's home, a hospital, or a physician's office. The programmer 606 may wirelessly communicate with the ICM 603 and utilize protocols, such as Bluetooth, GSM, infrared wireless LANs, HIPERLAN, 3G, satellite, as well as circuit and packet data protocols, and the like. Alternatively, a telemetry "wand" connection may be used to connect the programmer 606 to the ICM 603. The programmer 606 is able to acquire ECG 622 from surface electrodes on a person (e.g., ECGs), electrograms (e.g., EGM) signals from the ICM 603, and/or cardiac activity data, AF episode information, AF statistics, diagnostics, markers, cardiac signal waveforms, atrial heart rates, device settings from the ICM 603. The programmer 606 interfaces with the network 612, either via the internet, to upload the information acquired from the surface ECG unit 620, or the ICM 603 to the server 602.

The local monitoring device 608 interfaces with the communication system to upload to the server 602 one or more of cardiac activity data set, AF episode information, AF statistics, diagnostics, markers, cardiac signal waveforms, heart rates, sensitivity profile parameter settings and detection thresholds. In one embodiment, the surface ECG unit 620 and the ICM 603 have a bi-directional connection 624 with the local RF monitoring device 608 via a wireless connection. The local monitoring device 608 is able to acquire cardiac signals from the surface of a person, cardiac activity data sets and other information from the ICM 603, and/or cardiac signal waveforms, heart rates, and device settings from the ICM 603. On the other hand, the local monitoring device 608 may download the data and information discussed herein from the database 604 to the surface ECG unit 620 or the ICM 603.

The user workstation 610 may be utilized by a physician or medical personnel to interface with the network 612 to download cardiac activity data, QRS complex durations, RV-LV conduction times, LV-RV conduction times, VV CT differences and other information discussed herein from the database 604, from the local monitoring devices 608, 616, from the ICM 603 or otherwise. Once downloaded, the user workstation 610 may process the CA data in accordance with one or more of the operations described above. The user workstation 610 may upload/push settings (e.g., sensitivity profile parameter settings), ICM instructions, pacing mode settings, other information and notifications to the cell phone 614, local monitoring devices 608, 616, programmer 606, server 602 and/or ICM 603. For example, the user workstation 610 may provide instructions to the ICM 603 in order to update sensitivity profile parameter settings when the ICM 603 declares too many false AF detections.

The processes described herein in connection with analyzing cardiac activity data, determining intrinsic RV-LV intervals, determining RV-LV conduction times, determining LV-RV conduction times, the determining VV CT differences and setting pacing modes may be implemented by one or more of the devices illustrated in FIG. 6, including but not limited to the ICM 603, programmer 606, local monitoring devices 608, 616, user workstation 610, cell phone 614, and server 602. The process described herein may be distributed between the devices of FIG. 6.

In accordance with embodiments herein, methods and systems are described to automatically select between biventricular or LV single site only pacing. An automated procedure is described to determine preferred (e.g., optimal) device programming for effective BiV or LVSS fusion pacing. The methods and systems take advantage of interventricular electrical conduction time measurements across the RV and multiple LV electrodes to determine device programming.

Alternative Implementation Environments

Embodiments may be implemented in connection with one or more implantable medical devices (IMDs). Non-limiting examples of IMDs include one or more of transvenous devices, implantable leadless monitoring and/or therapy devices, neurostimulator devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. Additionally or alternatively, the IMD may be a leadless implantable medical device (LIMD) that include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

Additionally or alternatively, embodiments may be implemented with one or more subcutaneous IMDs that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. Further, one or more combinations of IMDs may be utilized from the above incorporated patents and applications in accordance with embodiments herein.

Additionally or alternatively, embodiments may be implemented with one or more IMDs that are leadless cardiac monitors (ICM) that include one or more structural and/or functional aspects of the device(s) described in U.S. Patent Application, U.S. patent application Ser. No. 15/084,373, filed Mar. 29, 2016, entitled, "METHOD AND SYSTEM TO DISCRIMINATE RHYTHM PATTERNS IN CARDIAC ACTIVITY," which are expressly incorporated herein by reference.

Additionally or alternatively, embodiments may be implemented with one or more IMD's that include one or more structural and/or functional aspects of the device as described in: U.S. patent application Ser. No. 15/973,126, titled "METHOD AND SYSTEM FOR SECOND PASS CONFIRMATION OF DETECTED CARDIAC ARRHYTHMIC PATTERNS"; U.S. patent application Ser. No. 15/973,351, titled "METHOD AND SYSTEM TO DETECT R-WAVES IN CARDIAC ARRHYTHMIC PATTERNS"; U.S. patent application Ser. No. 15/973,307, titled "METHOD AND SYSTEM TO DETECT POST VENTRICULAR CONTRACTIONS IN CARDIAC ARRHYTHMIC PATTERNS"; and U.S. patent application Ser. No. 16/399,813, titled "METHOD AND SYSTEM TO DETECT NOISE IN CARDIAC ARRHYTHMIC PATTERNS", which are expressly incorporated herein by reference.

All references, including publications, patent applications and patents, cited herein are hereby incorporated by reference to the same extent as if each reference were individually and specifically indicated to be incorporated by reference and were set forth in its entirety herein.

For example, embodiments may be implemented with two or more leadless IMDs implanted, one in the RV and one or more within the vasculature along the LV. As another example, embodiments may be implemented with a single chamber IMD having a transvenous lead in/proximate one of the RV or LV, while a leadless IMD is located in/proximate the other one of the LV or RV. As another example, embodiments may be implemented in connection with a combination of one or more IMD coupled to a transvenous lead, a leadless IMD, a subcutaneous IMD and the like.

The single chamber transvenous IMD, subcutaneous IMD, leadless IMD, or a combination thereof may be configured to operate in a BiV mode, a LV-MPP mode and a LVSS mode. The combination of the single chamber transvenous IMD, subcutaneous IMD, leadless IMD may perform the measurements, while one or more of the single chamber transvenous IMD, subcutaneous IMD, leadless IMD perform the analysis to select between the modes of operation. Additionally or alternatively, an external device may collect CA signals, device markers, timing information (generally referred to as measurements) from a multi-chamber transvenous IMD (of FIG. 1), a single chamber transvenous IMD, subcutaneous IMD(s), and leadless IMD(s). The external device may then perform the analysis to select between the operation modes of interest. One or more IMDs may measure the intrinsic, paced and sensed events of interest and provide one or both of the raw cardiac activity signals to the external device and/or device markers and timestamps indicative of when the intrinsic, paced and sensed events of interest occurred. When an external device is used to perform the analysis, the external device may wirelessly convey mode instructions to one or more IMDs to direct the one or more IMDs to operate in the selected mode. Closing The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A system, comprising:
   at least one implantable lead comprising a right ventricular (RV) electrode and one or more left ventricular (LV) electrodes;
   at least one processor; and
   a memory coupled to the at least one processor, wherein the memory stores program instructions, wherein the program instructions are executable by the at least one processor to:
   determine both of:
     i) a right ventricular to left ventricular (RV-LV) conduction time representative of a conduction time between a right ventricular (RV) paced or sensed event at the RV electrode and one or more responsive left ventricular (LV) sensed events at the LV electrode;
     ii) a left ventricular to right ventricular (LV-RV) conduction time representative of a conduction time between one or more LV paced or sensed events at the LV electrode and an RV sensed event at the RV electrode; or
   calculate a relation between a threshold and the RV-LV conduction time and the LV-RV conduction time; and
   set a pacing mode of an implantable medical device to one of i) a biventricular (BiV) pacing mode and ii) an LV only pacing mode based on the relation.

2. The system of claim 1, wherein the at least one processor is further configured to:
   when calculating the relation, compare the threshold to at least one of i) the RV-LV conduction time, ii) the LV-RV conduction time, or iii) a difference between the RV-LV and LV-RV conduction times; and when setting the pacing mode, to perform at least one of:
  i) set the pacing mode to the BiV pacing mode when the difference exceeds the threshold and to set the pacing mode to the LV only pacing mode when the difference equals or is below the threshold;
  ii) set the pacing mode to the BiV pacing mode when the RV-LV conduction time is below the threshold and to set the pacing mode to the LV only pacing mode when the difference equals or exceeds the threshold; or
  iii) set the pacing mode to the BiV pacing mode when the LV-RV conduction time is below the threshold and to set the pacing mode to the LV only pacing mode when the difference equals or exceeds the threshold.

3. The system of claim 1, wherein the at least one processor is further configured to calculate, as the relation, a mathematical relation between the RV-LV conduction time and the LV-RV conduction time, the pacing mode set based on the mathematical relation.

4. The system of claim 1, wherein the RV-LV conduction time represents the conduction time between an RV paced event and an LV sensed event (RVp-LVs), wherein the LV-RV conduction time represents the conduction time between an LV paced event and an RV sensed event (LVp-RVs), and wherein the relation represents a difference between the RVp-LVs conduction time and the LVp-RVs conduction time.

5. The system of claim 1, further comprising an LV lead having multiple LV electrodes configured to detect LV sensed events and to deliver LV paced events, wherein the at least one processor is further configured to:
  measure intrinsic RV/LV intervals between an RV intrinsic event, measured at the RV electrode, and LV intrinsic events, measured at the corresponding LV electrodes; and
  based on the measured intrinsic RV/LV intervals, select one of the LV electrodes as an LV pace/sense site to use to determine at least one of the RV-LV conduction time or the LV-RV conduction time.

6. The system of claim 5, wherein the LV pace/sense site selected represents at least one of:
  i) the one of the LV electrodes having a longest one of the RV-LV intrinsic conduction times; or
  ii) the LV pace/sense site represents a site of latest LV activation within the multiple LV electrodes.

7. The system of claim 1, wherein, during the LV only pacing mode, the at least one processor is configured to not pace in the RV.

8. The system of claim 1, wherein the at least one processor is further configured to time delivery of pacing pulses in the LV only pacing mode in a fusion timing manner with intrinsic conduction from the RV apex along the LV.

9. A system, comprising:
  at least one implantable lead comprising a right ventricular (RV) electrode and one or more left ventricular (LV) electrodes;
  at least one processor; and
  a memory coupled to the at least one processor, wherein the memory stores program instructions, wherein the program instructions are executable by the at least one processor to:
  determine at least one of:
    i) a right ventricular to left ventricular (RV-LV) conduction time representative of a conduction time between a right ventricular (RV) paced or sensed event and one or more responsive left ventricular (LV) sensed events; or
    ii) a left ventricular to right ventricular (LV-RV) conduction time representative of a conduction time between one or more LV paced or sensed events and an RV sensed event; or
  calculate a relation between a threshold and the at least one of the RV-LV conduction time or LV-RV conduction time; and
  set a pacing mode of an implantable medical device to one of i) a biventricular (BiV) pacing mode and ii) an LV only pacing mode based on the relation,
  wherein the at least one processor is further configured to identify a site of latest LV activation to be utilized to determine the at least one of RV-LV conduction time or the LV-RV conduction time.

10. A system, comprising:
  at least one implantable lead comprising a right ventricular (RV) electrode and one or more left ventricular (LV) electrodes;
  at least one processor; and
  a memory coupled to the at least one processor, wherein the memory stores program instructions, wherein the program instructions are executable by the at least one processor to:
  determine at least one of:
    i) a right ventricular to left ventricular (RV-LV) conduction time representative of a conduction time between a right ventricular (RV) paced or sensed event and one or more responsive left ventricular (LV) sensed events; or
    ii) a left ventricular to right ventricular (LV-RV) conduction time representative of a conduction time between one or more LV paced or sensed events and an RV sensed event; or
  calculate a relation between a threshold and the at least one of the RV-LV conduction time or LV-RV conduction time; and
  set a pacing mode of an implantable medical device to one of i) a biventricular (BiV) pacing mode and ii) an LV only pacing mode based on the relation,
  wherein the at least one processor is further configured to at least one of:
    i) time delivery of RV and LV pacing pulses in the BiV pacing mode in a fusion timing manner with intrinsic conduction in the RA; or
    ii) time delivery of pacing pulses in the LV only pacing mode in a fusion timing manner with intrinsic conduction from the RV apex along the LV.

11. A computer implemented arrhythmia detection method, comprising:
  under control of one or more processors configured with specific executable instructions, determining both of:
    i) a right ventricular to left ventricular (RV-LV) conduction time representative of a conduction time between a right ventricular (RV) paced or sensed event at an RV electrode and one or more responsive left ventricular (LV) sensed events at an LV electrode; and
    ii) a left ventricular to right ventricular (LV-RV) conduction time representative of a conduction time between one or more LV paced or sensed events at the LV electrode and an RV sensed event at the RV electrode; or
  calculating a relation between a threshold and the RV-LV conduction time and the LV-RV conduction time; and setting a pacing mode of an implantable medical device (IMD) to a select one of i) a biventricular (BiV) pacing mode and ii) an LV only pacing mode based on the relation.

12. The method of claim 11, further comprising, when calculating the relation, comparing the threshold to at least one of i) the RV-LV conduction time, ii) the LV-RV conduction time, or iii) a difference between the RV-LV and LV-RV conduction times; and when setting the pacing mode, to perform at least one of: i) setting the pacing mode to the BiV pacing mode when the difference exceeds the threshold and to set the pacing mode to the LV only pacing mode when the difference equals or is below the threshold; ii) setting the pacing mode to the BiV pacing mode when the RV-LV conduction time is below the threshold and to set the pacing mode to the LV only pacing mode when the difference equals or exceeds the threshold; or iii) setting the pacing mode to the BiV pacing mode when the LV-RV conduction time is below the threshold and to set the pacing mode to the LV only pacing mode when the difference equals or exceeds the threshold.

13. The method of claim 12, further comprising calculating, as the relation, a mathematical relation between the RV-LV conduction time and the LV-RV conduction time, the pacing mode set based on the mathematical relation.

14. The method of claim 11, further comprising:
detecting an RV intrinsic event;
detecting LV intrinsic events, associated with the RV intrinsic event, utilizing multiple LV electrodes;
measuring intrinsic RV-LV intervals between the RV intrinsic event, measured at the RV electrode, and the LV intrinsic events, measured at the corresponding LV electrodes; and
based on the measured intrinsic RV-LV intervals, setting a configuration mode of the IMD to utilize one of the LV electrodes as an LV pace/sense site when determining the RV-LV conduction time and the LV-RV conduction time.

15. The method of claim 14, wherein the LV pace/sense site selected represents the one of the LV electrodes having a longest one of the RV-LV intrinsic conduction times.

16. The method of claim 11, further comprising identifying a site of latest LV activation to be utilized to determine the RV-LV conduction time and the LV-RV conduction time.

17. The method of claim 11, wherein, during the LV only pacing mode, the IMD is configured to not pace in the RV.

18. The method of claim 11, further comprising timing delivery of RV and LV pacing pulses in the BiV pacing mode in a fusion timing manner with intrinsic conduction from the RA.

19. The method of claim 11, further comprising timing delivery of pacing pulses in the LV only pacing mode in a fusion timing manner with intrinsic conduction from the RV apex along the LV.

20. A computer implemented arrhythmia detection method, comprising:
under control of one or more processors configured with specific executable instructions, determining at least one of:
i) a right ventricular to left ventricular (RV-LV) conduction time representative of a conduction time between a right ventricular (RV) paced or sensed event and one or more responsive left ventricular (LV) sensed events; or
ii) a left ventricular to right ventricular (LV-RV) conduction time representative of a conduction time between one or more LV paced or sensed events and an RV sensed event; or
calculating a relation between a threshold and the at least one of the RV-LV conduction time or LV-RV conduction time; and
setting a pacing mode of an implantable medical device (IMD) to a select one of i) a biventricular (BiV) pacing mode and ii) an LV only pacing mode based on the relation,
wherein the LV pace/sense site represents a site of latest LV activation within the multiple LV electrodes.

* * * * *